US012685804B2

(12) United States Patent
Harley et al.

(10) Patent No.: US 12,685,804 B2
(45) Date of Patent: Jul. 21, 2026

(54) COMPOSITE MATERIALS AND METHODS OF MAKING AND USING THE SAME

(71) Applicants: The Board of Trustees of the University of Illinois, Urbana, IL (US); The Regents of the University of California, Oakland, CA (US)

(72) Inventors: Brendan A. C. Harley, Urbana, IL (US); Marley J. Dewey, Champaign, IL (US); Justine Lee, Los Angeles, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 70 days.

(21) Appl. No.: 18/418,012

(22) Filed: Jan. 19, 2024

(65) Prior Publication Data

US 2024/0408280 A1     Dec. 12, 2024

Related U.S. Application Data

(60) Provisional application No. 63/440,325, filed on Jan. 20, 2023.

(51) Int. Cl.
| | |
|---|---|
| *A61L 27/56* | (2006.01) |
| *A61L 27/12* | (2006.01) |
| *A61L 27/20* | (2006.01) |
| *A61L 27/24* | (2006.01) |
| *A61L 27/36* | (2006.01) |

(52) U.S. Cl.
CPC ............... *A61L 27/56* (2013.01); *A61L 27/12* (2013.01); *A61L 27/20* (2013.01); *A61L 27/24* (2013.01); *A61L 27/365* (2013.01)

(58) Field of Classification Search
None
See application file for complete search history.

(56) References Cited

U.S. PATENT DOCUMENTS

| | | | | |
|---|---|---|---|---|
| 7,022,522 B2 * | 4/2006 | Guan | ...................... | A61L 27/46 |
| | | | | 435/395 |
| 8,647,393 B2 * | 2/2014 | Marshall | ................. | A61L 27/56 |
| | | | | 623/23.74 |
| 10,166,316 B2 | 1/2019 | Landon et al. | | |
| 10,317,395 B1 * | 6/2019 | Singh | ................. | G01N 33/5052 |

(Continued)

FOREIGN PATENT DOCUMENTS

| | | |
|---|---|---|
| WO | WO 2006/095154 | 9/2006 |
| WO | WO 2006/115892 | 11/2006 |

(Continued)

OTHER PUBLICATIONS

Herath et al. Mechanical and geometrical study of 3D printed Voronoi scaffold design for large bone defects. Materials & Design. vol. 212 Dec. 2021 (Year: 2021).*

(Continued)

*Primary Examiner* — Cachet I Proctor
(74) *Attorney, Agent, or Firm* — Klarquist Sparkman, LLP

(57) ABSTRACT

Composite materials including a macroporous structure having a Voronoi architecture and a microporous biomaterial integrated into the macroporous structure are provided. Methods of making the composite materials and methods of using the materials to treat a bone defect are also provided.

17 Claims, 14 Drawing Sheets

100

102

104

106

(56)                    References Cited

U.S. PATENT DOCUMENTS

| | | | | |
|---|---|---|---|---|
| 10,517,993 | B2 * | 12/2019 | Iwai | A61L 27/56 |
| 2005/0214340 | A1 * | 9/2005 | Erbe | A61B 17/80 623/16.11 |
| 2009/0157182 | A1 * | 6/2009 | Koblish | A61F 2/28 623/23.72 |
| 2019/0046322 | A1 * | 2/2019 | Moore | A61F 2/3859 |
| 2020/0315772 | A1 * | 10/2020 | Rocco | A61F 2/08 |

FOREIGN PATENT DOCUMENTS

| | | |
|---|---|---|
| WO | WO 2007/103993 | 9/2007 |
| WO | WO 2021/009515 | 1/2021 |

OTHER PUBLICATIONS

Al-Munajjed et al., "Development of a Collagen Calcium-Phosphate Scaffold as a Novel Bone Graft Substitute," *Studies in Health Technology and Informatics*, (Feb. 2008), (13 pages).

Al-Munajjed et al., "Development of a Biomimetic Collagen-Hydroxyapatite Scaffold for Bone Tissue Engineering Using a SBF Immersion Technique," *Journal of Biomedical Materials Research Part B: Applied Biomaterials*, vol. 90, No. 2, pp. 584-591, (2009), (29 pages).

Aurenhammer et al., "Voronoi Diagrams," *Handbook of Computational Geometry*, vol. 5, No. 10, pp. 1-101 (2000), (101 pages).

Bose et al., "Recent Advances in Bone Tissue Engineering Scaffolds," *Trends in Biotechnology*, vol. 30, No. 10, pp. 1-18, (Oct. 2012), (18 pages).

Chang et al., "Tough and Tunable Scaffold-Hydrogel Composite Biomaterial for Soft-to-Hard Musculoskeletal Tissue Interfaces," *Science Advances*, vol. 6, No. 34, pp. 1-10, (Aug. 19, 2020), (10 pages).

Chen et al., "Porous Scaffold Design for Additive Manufacturing in Orthopedics: A Review," *Frontiers in Bioengineering and Biotechnology*, vol. 8, No. 609, pp. 1-20, (Jun. 17, 2020), (20 pages).

Cunniffe et al., "Development and Characterization of Collagen Nano-Hydroxyapatite Composite Scaffold for Bone Tissue Engineering," *Journal of Materials Science: Materials in Medicine*, vol. 21, No. 8, pp. 2293-2298, (Aug. 2010), (16 pages).

Curtin et al., "Innovative Collagen Nano-Hydroxyapatite Scaffolds Offer Highly Efficient Non-Viral Gene Delivery Platform for Stem Cell-Mediated Bone Formation," *Advanced Materials*, vol. 24, pp. 749-754, (2012), (6 pages).

Dewey et al., "Shape-Fitting Collagen-PLA Composite Promotes Osteogenic Differentiation of Porcine Adipose Stem Cells," *Journal of the Mechanical Behavior of Biomedical Materials*, vol. 95, pp. 21-33, (2019), (39 pages).

Dewey et al., "Anisotropic Mineralized Collagen Scaffolds Accelerate Osteogenic Response in a Glycosaminoglycan-Dependent Fashion," *RSC Advances*, vol. 10, No. 26, pp. 15629-15641, (2020), (13 pages).

Dewey et al., "Inclusion of a 3D-printed Hyperelastic Bone Mesh improves Mechanical and Osteogenic Performance of a Mineralized Collagen Scaffold," *Acta Biomaterialia*, vol. 121, pp. 224-236, (Feb. 2021), (29 pages).

Dimitriou et al., "Biomaterial Osseointegration Enhancement with Biophysical Stimulation," *Journal of Musculoskeletal Neuronal Interactions*, vol. 7, No. 3, pp. 253-265, (2007), (13 pages).

Florent et al., "Enhanced Bone Healing Using Collagen-Hydroxyapatite Scaffold Implantation in the Treatment of a Large Multiloculated Mandibular Aneurysmal Bone Cyst in a Thoroughbred Filly," *Journal of Tissue Engineering and Regenerative Medicine*, vol. 9, pp. 1193-1199, (2015), (7 pages).

Gibson et al., "Cellular Materials in Nature and Medicine," *Cambridge University Press*, 9 pages, (2010), (9 pages).

Ghosh et al., Multiple Scale Analysis of Heterogeneous Elastic Structures Using Homogenization Theory and Voronoi Cell Finite Element Method, *International Journal of Solids and Structures*, vol. 32, No. 1, pp. 27-62, (1995), (36 pages).

Gómez et al. "Design and Properties of 3D Scaffolds for Bone Tissue Engineering," *Acta Biomaterialia*, vol. 42, pp. 341-350, (Sep. 15, 2016), (10 pages).

Haleem et al., "Role of CT and MRI in the Design and Development of Orthopaedic Model Using Additive Manufacturing," *Journal of Clinical Orthopaedics and Trauma*, vol. 9, pp. 213-217, (2018), (5 pages).

Hale et al., "Combat Casualty Care Lessons Learned from OEF and OI," *Office of the Surgeon General*, pp. 225-297, (2012), (73 pages).

Harley et al., "Mechanical Characterization of Collagen-Glycosaminoglycan Scaffolds," *Acta Biomaterialia*, vol. 3, pp. 463-474, (2007), (12 pages).

Harley et al., "Design of a Multiphase Osteochondral Scaffold. II. Fabrication of a Mineralized Collagen-Glycosaminoglycan Scaffold," *Journal of Biomedical Materials Research*, pp. 1066-1077, (2010), (12 pages).

Hollister et al., "Engineering Craniofacial Scaffolds," *Orthodontics & Craniofacial Research*, vol. 8, Issue 3, pp. 162-173 (2005), (12 pages).

Hollister, "Porous Scaffold Design for Tissue Engineering," *Nature Materials*, vol. 4, pp. 518-524 (Jul. 2005), (9 pages).

Hoyer et al., "Biomimetically Mineralized Salmon Collagen Scaffolds for Application in Bone Tissue Engineering," *Biomacromolecules*, vol. 13, pp. 1059-1066. (2012), (8 pages).

Huang et al., "Three-Dimensionally Printed Hyperelastic Bone Scaffolds Accelerate Bone Regeneration in Critical-Size Calvarial Bone Defects," *American Society of Plastic Surgeons*, vol. 143, No. 5, pp. 1397-1407 (May 2019), (12 pages).

Jardini et al., "Cranial Reconstruction: 3D Biomodel and Custom-Built Implant Created Using Additive Manufacturing," *Journal of Cranio-Maxillofacial Surgery*, vol. 42, No. 8, pp. 1877-1884 (2014), (25 pages).

Kanungo et al., "Characterization of Mineralized Collagen-Glycosaminoglycan Scaffolds for Bone Regeneration," *Acta Biomaterialia*, vol. 4, pp. 490-503 (2008), (14 pages).

Kolliopoulos et al., "Amnion and Chorion Matrix Maintain hMSC Osteogenic Response and Enhance Immunomodulatory and Angiogenic Potential in Mineralized Collagen Scaffold," *Frontiers in Bioengineering and Biotechnology*, pp. 1-16, (Nov. 14, 2022), (16 pages).

Lee et al., "Optimizing Collagen Scaffolds for Bone Engineering: Effects of Cross-linking and Mineral Content on Structural Contraction and Osteogenesis," *Journal of Craniofacial Surgery*, vol. 26, No. 6, pp. 1992-1996 (Sep. 2015), (15 pages).

Lew et al., "Characterization of Craniomaxillofacial Battle Injuries Sustained by United States Service Members in the Current Conflicts of Iraq and Afghanistan," *Journal of Oral and Maxillofacial Surgery*, vol. 68, pp. 3-7 (2010), (7 pages).

Lyons et al., "Novel Microhydroxyapatite Particles in a Collagen Scaffold: A Bioactive Bone Void Filler?," *Clinical Orthopaedics and Related Research*, vol. 472, pp. 1318-1328 (2014), (11 pages).

Martínez et al., "Procedural Voronoi Foams for Additive Manufacturing," *ACM Transactions on Graphics*, vol. 35, pp. 1-12, (2016), (13 pages).

Mitsak et al., "Effect of Polycaprolactone Scaffold Permeability on Bone Regeneration In Vivo," *Tissue Engineering Part A*, pp. 1831-1839 (2011), (10 pages).

Morrison et al., "Mitigation of Tracheobronchomalacia with 3D-printed Personalized Medical Devices in Pediatric Patients," *Science Translational Medicine*, vol. 7, No. 285, pp. 1-23 (2015), (23 pages).

Ott et al., "An Introduction to Statistical Methods and Data Analysis," *Cengage Learning*, 16 pages, (2016), (16 pages).

Quinlan et al., "Development of Collagen-Hydroxyapatite Scaffolds Incorporating PLGA and Alginate Microparticles for the Controlled Delivery of rhBMP-2 for Bone Tissue Engineering," *Journal of Controlled Release: Official Journal of the Controlled Release Society*, (2015), (27 pages).

Ren et al., "Osteogenesis on Nanoparticulate Mineralized Collagen Scaffolds via Autogenous Activation of the Canonical BMP Receptor Signaling Pathway," *Biomaterials*, vol. 50, pp. 107-114 (May 2015), (19 pages).

Ren et al., "Nanoparticulate Mineralized Collagen Scaffolds and BMP-9 Induce a Long-Term Bone Cartilage Construct in Human

(56) References Cited

OTHER PUBLICATIONS

Mesenchymal Stem Cells," *Advanced Healthcare Materials*, vol. 5, No. 14, pp. 1821-1830 (Jul. 2016), (20 pages).

Ren et al., "Nanoparticulate Mineralized Collagen Scaffolds Induce In Vivo Bone Regeneration Independent of Progenitor Cell Loading or Exogenous Growth Factor Stimulation," *Biomaterials*, vol. 89, pp. 67-78 (2016), (26 pages).

Roberts et al., "Elastic Moduli of Model Random Three-Dimensional Closed-Cell Cellular Solids," *Acta Materialia*, vol. 49, Issue 2, pp. 189-197, (2001), (13 pages).

Schon et al., "Individually Preformed Titanium Mesh Implants for a True-to-Original Repair of Orbital Fractures," *International Journal of Oral & Maxillofacial Surgery*, vol. 35, pp. 990-995, (2006), (6 pages).

Shamos et al., "Closest-Point Problems," *6th Annual Symposium on Foundations of Computer Science*, pp. 151-162, (1975), (12 pages).

Seong et al., "Calcium Phosphate-Collagen Scaffold with Aligned Pore Channels for Enhanced Osteochondral Regeneration," *Advanced Healthcare Materials*, vol. 6, (2017), (11 pages).

Terjesen et al., "Bone Atrophy After Plate Fixation: Computer Tomography of Femoral Shaft Fractures," *Acta Orthopaedica Scandinavica*, vol. 56, pp. 416-418, (1985), (4 pages).

Tiffany et al., "The Inclusion of Zinc into Mineralized Collagen Scaffolds for Craniofacial Bone Repair Applications," *Acta Biomaterialia*, vol. 93, pp. 86-96, (Jul. 15, 2019), (11 pages).

Tiffany et al. "Sequential Sequestrations Increase the Incorporation and Retention of Multiple Growth Factors in Mineralized Collagen Scaffolds," *RSC Advances*, vol. 10, No. 45, pp. 26982-26996. (Jul. 15, 2020), (15 pages).

Vajjhala et al., "A Cellular Solid Model for Modulus Reduction Due to Resorption of Trabeculae in Bone," *Journal of Biomechanical Engineering*, vol. 122, pp. 511-515 (Oct. 2000), (5 pages).

Wang et al., "Advanced Reconfigurable Scaffolds Fabricated by 4D Printing for Treating Critical-Size Bone Defects of Irregular Shapes," *Biofabrication*, vol. 12, (2020), (16 pages).

Weisgerber et al., "A Mineralized Collagen-Polycaprolactone Composite Promotes Healing of a Porcine Mandibular Defect," *Tissue Engineering: Part A*, vol. 24, No. 11 & 12, pp. 943-954, (2018), (12 pages).

Weisgerber et al., "Mineralized Collagen Scaffolds Induce hMSC Osteogenesis and Matrix Remodeling," *Biomaterials Science*, vol. 3, No. 3, (2015), (21 pages).

Weisgerber et al., "Evaluation of Multi-Scale Mineralized Collagen-Polycaprolactone Composites for Bone Tissue Engineering," *Journal of the Mechanical Behavior of Biomedical Materials*, vol. 61, (2016), (31 pages).

Woodruff et al., "The Return of a Forgotten Polymer: Polycaprolactone in the 21 st Century," *Progress in Polymer Science*, vol. 35, Issue 10, (2010), (103 pages).

Youssef et al., "Additive Manufacturing of Polymer Melts for Implantable Medical Devices and Scaffolds," *International Society for Biofabrication*, vol. 9, (2017), (30 pages).

Xie et al., "Self-Fitting Shape Memory Polymer Foam Inducing Bone Regeneration: A Rabbit Femoral Defect Study," *Biochimica et Biophysica Acta. General Subjects*, pp. 936-945 (2018), (10 pages).

Zhang et al., "A Bioactive "Self-Fitting" Shape Memory Polymer Scaffold with Potential to Treat Cranio-Maxillo Facial Bone Defects," *Biofabrication*, vol. 9, (2017), (9 pages).

Zhao et al., "Design and Mechanical Properties Verification of Gradient Voronoi Scaffold for Bone Tissue Engineering," *Micromachines*, vol. 12, No. 6, pp. 1-23, (Jun. 5, 2021), (23 pages).

Zhou et al., "Stiffness of Nanoparticulate Mineralized Collagen Scaffolds Triggers Osteogenesis via Mechanotransduction and Canonical Wnt Signaling," *Macromolecular Bioscience*, vol. 21, No. 3, (Mar. 2021), (27 pages).

* cited by examiner

Objective 1: Alter the porosity of Voronoi structures to achieve various mechanical properties Investigating:
-Strut thickness
-Pore spacing
-Isotropy vs. vs.

Objective 2: Create mineralized collagen scaffolds reinforced with biphasic Voronoi 3D-prints Mineralized collagen scaffold

+

Porous    Dense

Biphasic 3D-print

Investigating:
-Strain concentrations

Objective 3: Evaluate shape-fitting and osteogenesis of 2D and 3D Voronoi composite sheets Mineralized collagen scaffold

+

Voronoi 3D-printed sheet

Investigating:
-Shape-fitting through push-out testing
-Handling of sheets

FIG. 2A

1. Random "seed" points are generated throughout any shape

2. Phantom lines are drawn between every point for guidance

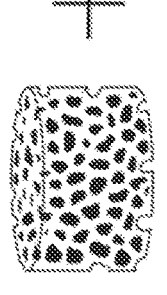

3. The pore walls are drawn at the midpoint of each of these phantom lines to create the Voronoi structure 4. The result is the starting shape filled with a random open-porous network FIG. 4
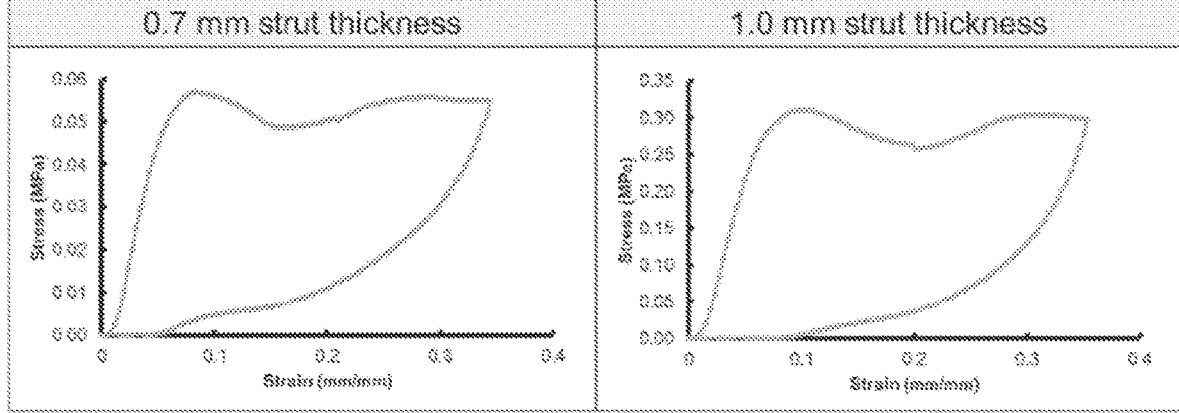
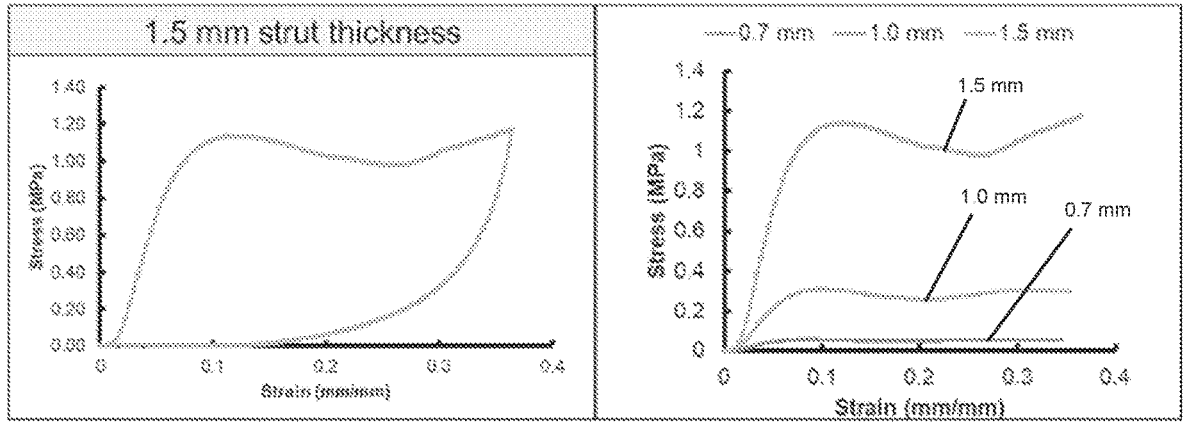

FIG. 5A                    FIG. 5B
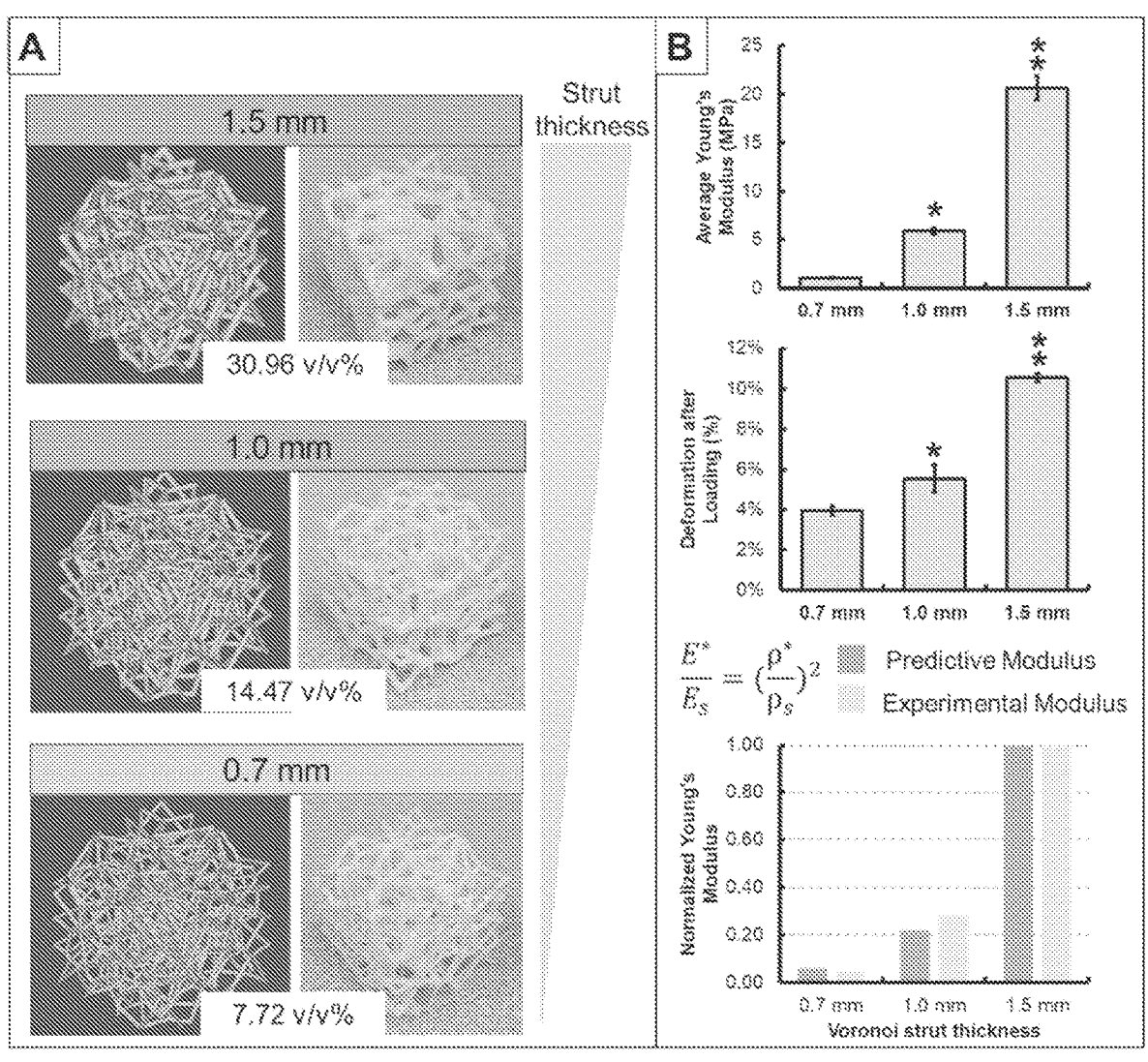

FIG. 7A                    FIG. 7B
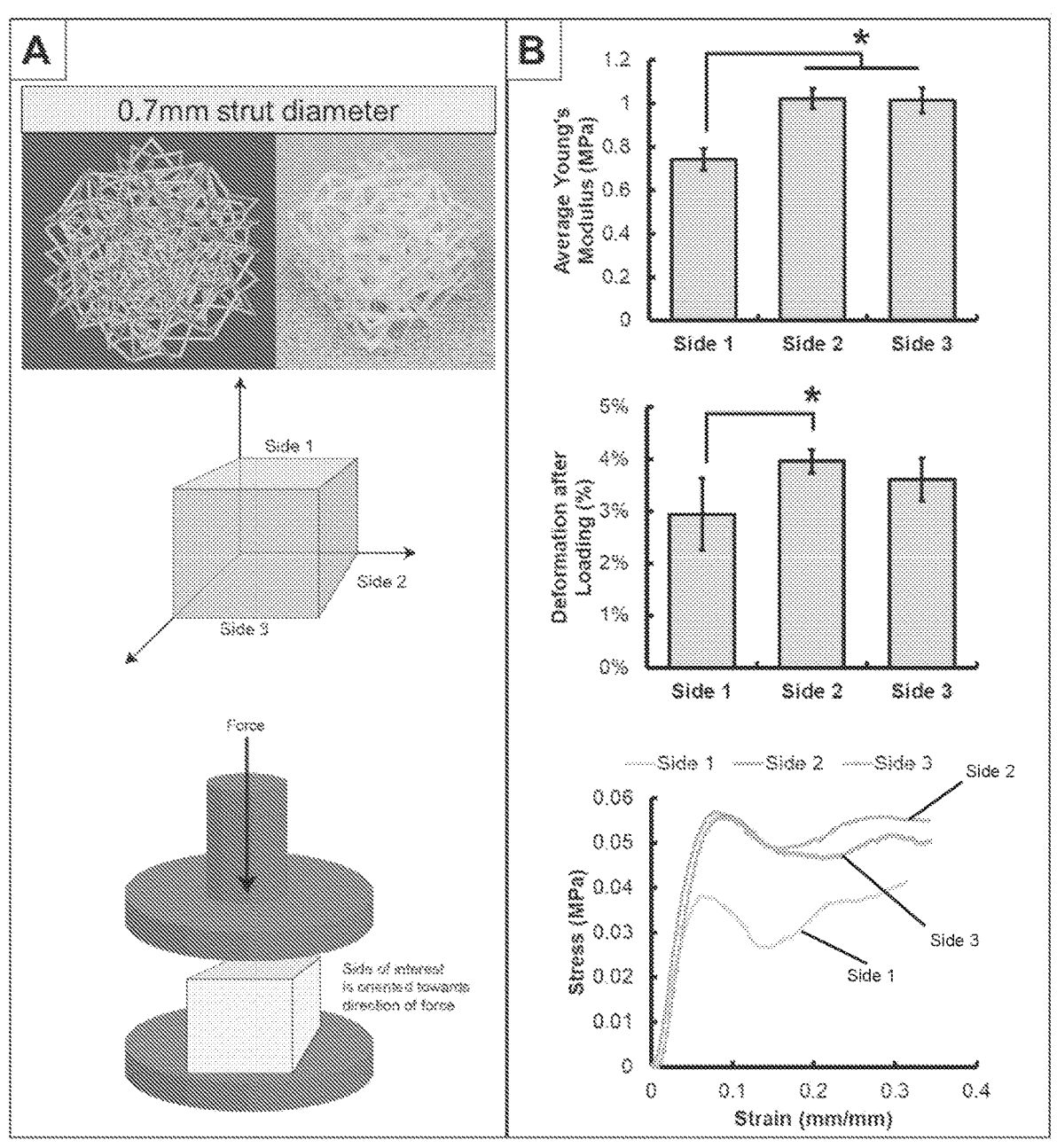

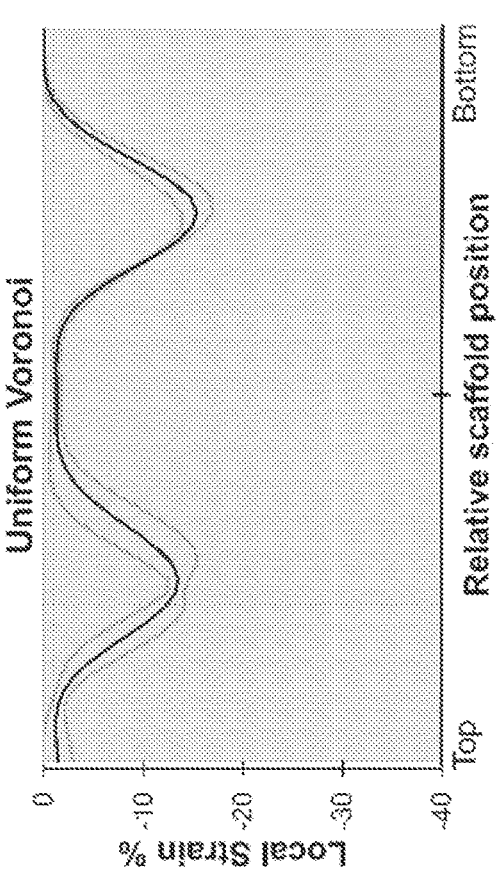
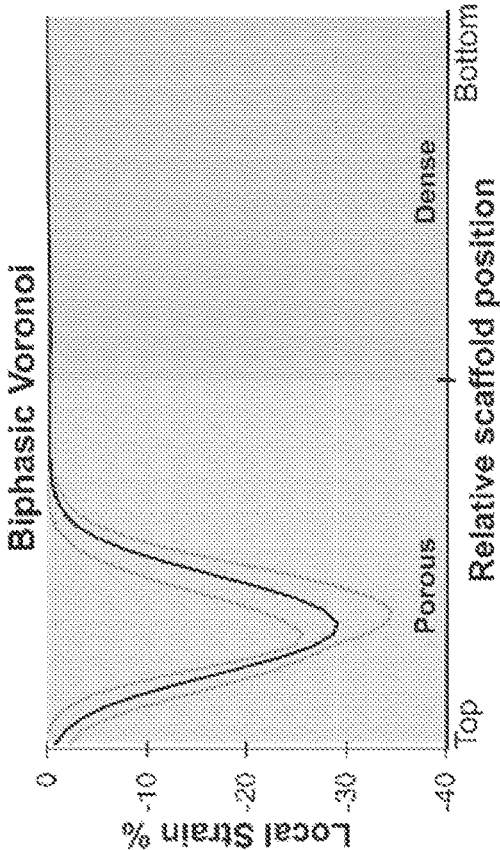
FIG. 11

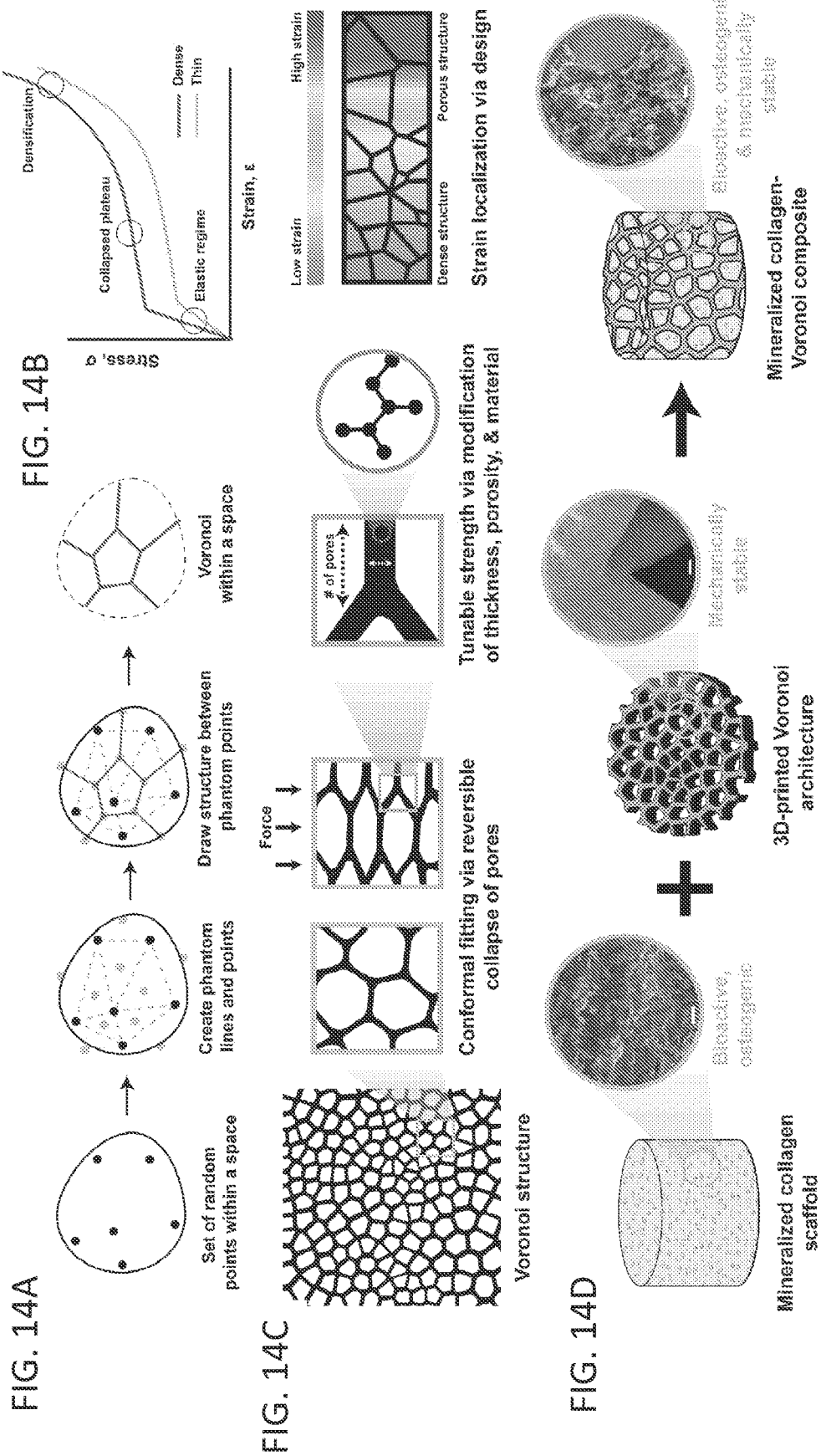

COMPOSITE MATERIALS AND METHODS OF MAKING AND USING THE SAME

CROSS REFERENCE TO RELATED APPLICATION

This application claims the benefit of U.S. Provisional Application No. 63/440,325, filed Jan. 20, 2023, which is incorporated herein by reference in its entirety.

ACKNOWLEDGMENT OF GOVERNMENT SUPPORT

This invention was made with government support under Grant No. W81XWH-16-1-0566 awarded by the United States Army/Army Medical Research and Material Command, and Grant Nos. R01 DE030491 and R21 DE026582 awarded by the National Institutes of Health. The government has certain rights in the invention.

FIELD

This disclosure relates to composite materials and methods of their use, for example in methods of repairing bone defects.

BACKGROUND

Creating biomaterials to repair missing segments of bone is challenging not only due to the variety of cell types involved in bone regeneration, but also the complex mechanical properties. Craniomaxillofacial (CMF) defects are especially difficult to repair due to the substantial amount of bone missing, which will not regenerate without surgical intervention. Examples of these include cleft palate birth defects, loss of bone volume from dentures and cancer resection, and battlefield injuries. Many of these defects are irregular in size and shape, especially if these result from birth defects and trauma injuries. Thus, the repair of these defects not only requires a material able to promote new bone formation, but one that can be designed for any size and shape. Additionally, these must be stiff enough to promote new bone formation, but also fit well to the defect site during implantation and be easy for the surgeon to handle. This creates the need for very precise design of the mechanical properties of biomaterials.

SUMMARY

Disclosed herein are composite materials with properties that make them particularly useful for repair of irregular bone defects, such as CMF defects. Also provided are methods of making and using the disclosed materials.

In some embodiments, a composite material including a macroporous structure having a Voronoi architecture and a microporous biomaterial integrated into the macroporous structure are provided. Embodiments of the composite material include a macroporous structure that is a mesh including a plurality of pores. In some examples, the macroporous structure includes fibers connecting points defining the Voronoi architecture. In embodiments, the composite material includes a macroporous structure with at least a first portion and a second portion, and wherein the pore size of the first portion is greater than the pore size of the second portion. The macroporous structure may be two-dimensional or three-dimensional.

In some embodiments, the biomaterial included in the composite material includes collagen, glycosaminoglycans, calcium phosphate, or a combination of two or more thereof. In one example, the biomaterial is mineralized collagen.

Also provided are methods of making the composite material. In some examples, the method includes contacting a macroporous structure having a Voronoi architecture with a solution including a liquid suspension of a biomaterial and removing the liquid from the solution, for example by lyophilization. The methods may also further include preparing and/or designing the macroporous structure. In some examples, the macroporous structure is produced using an additive manufacturing method.

In some embodiments, the disclosed composite materials are used to treat a bone defect in a subject. The methods include implanting the composite material in the bone defect. In some examples, the bone defect is a craniomaxillofacial bone defect. In some examples, the methods also include shaping the composite material to the bone defect of the subject prior to implanting the composite material.

The foregoing and other features of the disclosure will become more apparent from the following detailed description, which proceeds with reference to the accompanying figures.

BRIEF DESCRIPTION OF THE DRAWINGS

FIGS. 2A and 2B are schematics depicting exemplary Voronoi structures (FIG. 2A) and exemplary objectives of the current disclosure (FIG. 2B).

FIG. 3A is a schematic showing four Voronoi cube designs (10 mm side length) printed with photopolymerizable white resin and their design labels. FIG. 3B shows data from mechanical compression of Voronoi cubes to yield a Young's Modulus. Predictive modulus was compared to experimental modulus of each resin to demonstrate validity of the predictive modulus equation. X-axis denotes design labels in FIG. 3A FIG. 4 is a series of graphs showing representative compressive loading and unloading curves for laser-sintered PCL Voronoi cubes (25 mm side length). The bottom right graph is a representative stress-strain curve of laser-sintered PCL Voronoi cubes of different thicknesses overlaid on the same graph.

FIGS. 5A and 5B show the effect of strut thickness on mechanical behavior of Voronoi structures. FIG. 5A shows Voronoi cube structures (25 mm side length) made of laser-sintered PCL compared to their .stl design. FIG. 5B shows Voronoi cubes that were compressively loaded and unloaded to determine Young's Modulus and percent deformation after loading. The normalized Young's Modulus of the predictive equation was compared to the normalized Young's Modulus of experimental data. ** indicates the 1.5 mm group is significantly ($p < 0.05$) greater than the other two groups. * indicates the 1.0 mm group is significantly ($p < 0.05$) greater than the 0.7 mm group. Data represented as average±standard deviation.

FIG. 6A is a 3D rendering of biphasic Voronoi design, including a denser region and a porous region. FIG. 6B shows the biphasic Voronoi 3D-print made of white photo-polymerizable resin (left), mineralized collagen scaffolds (center), and a mineralized collagen scaffold reinforced with the biphasic Voronoi 3D-print (right). FIG. 6C shows SEM images of mineralized collagen infill into biphasic Voronoi 3D-prints. 1) represents the dense 3D-print region, in which there are areas where the collagen was unable to infiltrate. 2) represents the porous 3D-print region, in which it is visible that porous mineralized collagen surrounds the 3D-print and both are well-integrated.

FIGS. 7A and 7B show analysis of isotropy in Voronoi structures of various thicknesses. FIG. 7A schematically illustrates Voronoi cube structures with 0.7 mm strut diameter (25 mm side length) made of laser-sintered PCL are compressively loaded and unloaded on each of the three axis represented as side 1-3. FIG. 7B shows Young's modulus and percent deformation compared between the three compressed axes. A representative stress-strain curve of the three groups tested demonstrates loading behavior. * indicates one group is significantly (p<0.05) greater than another indicated group. Data are represented as average±standard deviation.

FIG. 8A is a representative stress-strain curve of Voronoi biphasic 3D-prints under compression. Numbers on the curve represent images of the compressed print on the right. The curve is broken into two segments, an area of strain density on the "porous" region of the 3D-print and an area of strain density on the "dense" region of the 3D-print. FIG. 8B shows stress-strain curves of the porous and dense regions of the biphasic 3D-print, demonstrating the elastic regimes, collapsed plateaus, densification regimes, and for the porous 3D-print, catastrophic failure. 3D-prints measured 20 mm×6 mm×6 mm (length×height×width).

FIG. 9A is a graph of Young's Modulus of mineralized collagen scaffold, the porous and dense region of the biphasic Voronoi 3D-print, the porous and dense region of the mineralized collagen scaffold reinforced with a biphasic Voronoi 3D-print. All groups are significantly different (p<0.05) from each other. Data are expressed as average±standard deviation (n=8). FIG. 9B shows a representative stress-strain curve of biphasic Voronoi 3D-prints. FIG. 9C is a graph of predictive and experimental modulus (E*) of rectangular Voronoi 3D-Prints. The normalized Young's modulus of the porous and dense region of the biphasic print and the Young's modulus of a uniform rectangular Voronoi print were all compared to the predictive normalized moduli based on cube Voronoi structures printed with the same material (see FIG. 6A) (n=8). FIG. 9D is a representative stress-strain curve of mineralized collagen reinforced with biphasic Voronoi 3D-print.

FIG. 11 shows line scans of the strain on biphasic Voronoi composite and uniform Voronoi composite from FIG. 10 were created from Digital Image Correlation data. Average strain at a global applied 4.4% strain was plotted as a function of position for each sample, with the average (black line) and standard deviation (interval contained by gray lines) of strain magnitude along the entire length of each scaffold. The porous region is demonstrated by a grey background and the dense region with green (n=6).

Figures 12A, 12B:
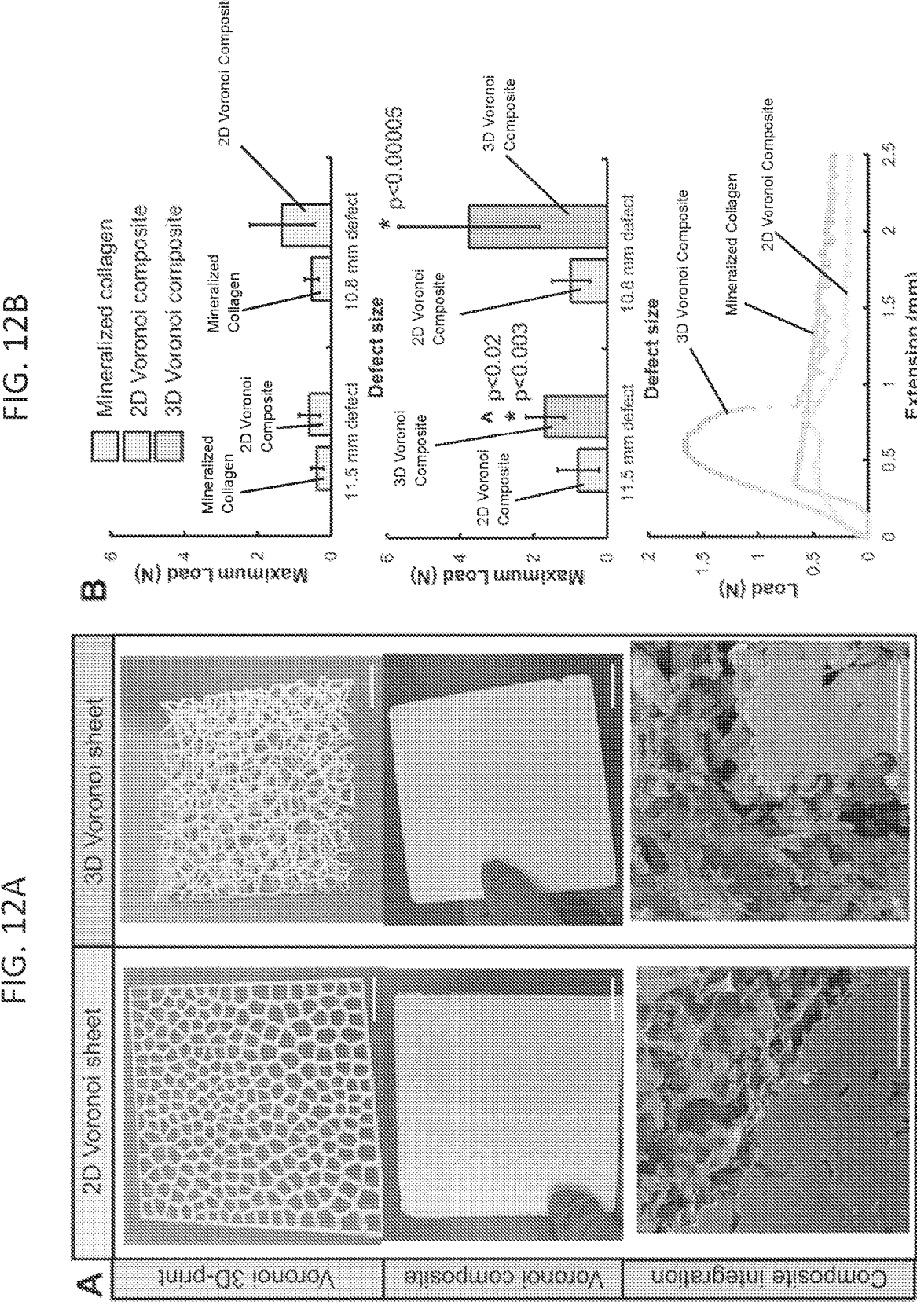

FIGS. 12A and 12B illustrate shape-fitting ability and fabrication of 2D and 3D Voronoi-mineralized collagen composite sheets. FIG. 12A is images of 2D and 3D Voronoi composites and 3D-prints. The Voronoi 3D-print row includes images of PCL 3D-printed sheets. Scale bar represents 15 mm. The Voronoi composite row includes images of the PCL 3D-print combined with mineralized collagen to create a composite material. Scale bar represents 15 mm. The composite integration row includes representative SEM images of the PCL 3D-print within the mineralized collagen scaffolds demonstrating integration of the 3D-print with surrounding collagen. Images are false colored blue to represent PCL 3D-print and red/yellow to represent mineralized collagen. SEM scale bar represents 250 μm. FIG. 12B shows push-out testing of mineralized collagen scaffolds, 2D Voronoi-collagen composites, and 3D Voronoi-collage composites. Push-out testing was performed on two cylindrical defect sizes (11.5 mm diameter and 10.8 mm diameter). There were no significant (p<0.05) differences in the pushout force required by the 2D Voronoi composite and the mineralized collagen scaffold. * indicates significant difference between the 3D Voronoi composite and the mineralized collagen scaffold at the respective defect size. ^indicates significant difference between the 3D Voronoi composite between the two defect sizes. The last figure includes a representative load vs. extension curve for the composites and mineralized collagen scaffolds in the 11.5 mm defect size. Data are represented as average±standard deviation (n=8).

Figure 13:
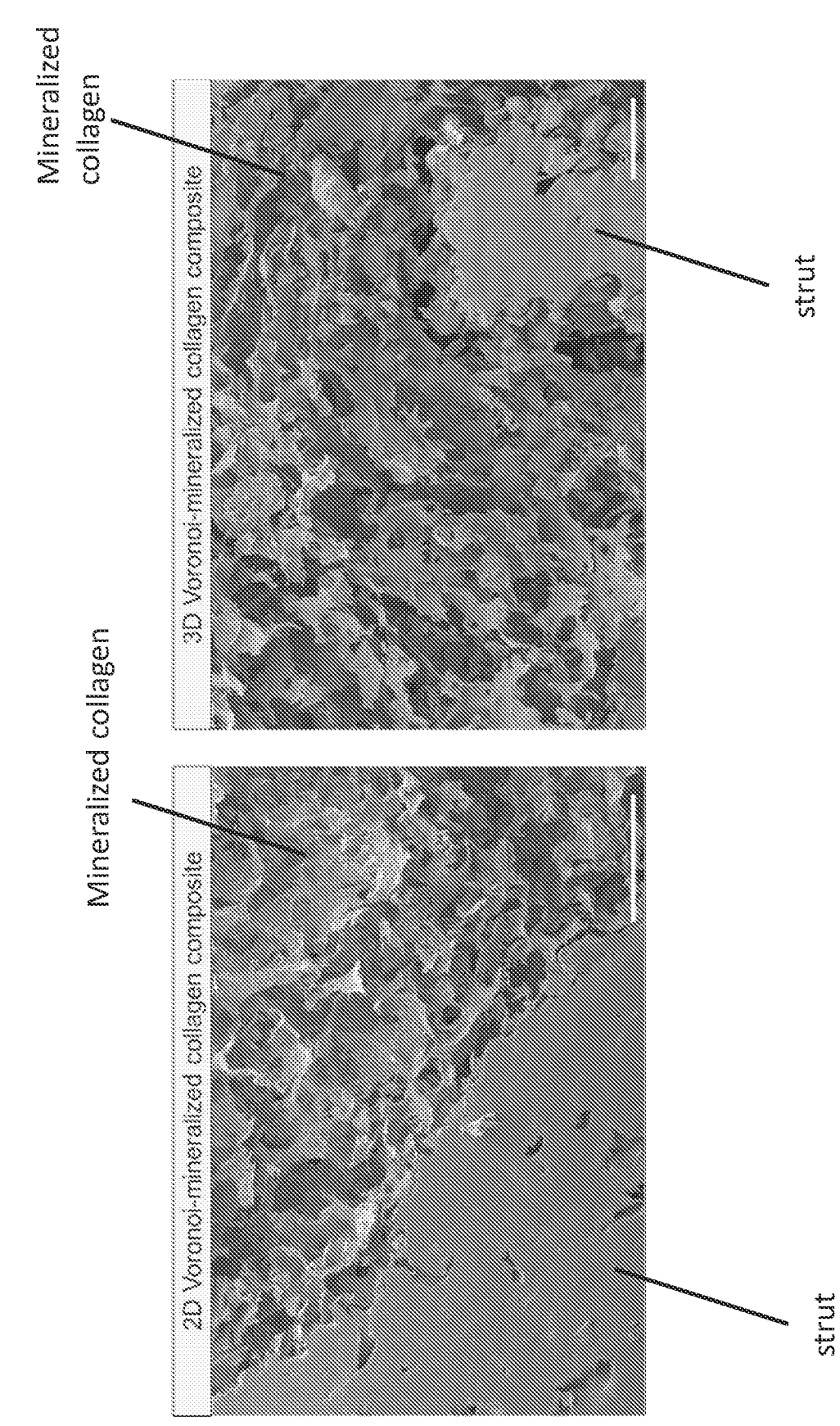

FIG. 13 is additional SEM images demonstrating integration of PCL 3D-print and mineralized collagen in 2D (left) and 3D (right) Voronoi-mineralized collagen composites. Scale bar represents 250 μm.

FIGS. 14A-14D is a schematic showing an exemplary overview of an embodiment. FIG. 14A shows creating a Voronoi structure within any space. First, a set of "seed" points are added to the space. Then phantom lines (green) are drawn between these points, with phantom points (green) in the middle of these areas. Finally, the lines of the Voronoi structure (blue) are drawn between the phantom lines connecting the phantom points. FIG. 14B shows representative stress-strain curve of foams, such as Voronoi structures. These structures are characterized by a linear elastic regime, a collapsed plateau, and densification. Increasing the density of Voronoi structures increases the modulus (elastic regime). FIG. 14C shows that Voronoi structures can be added to any size or shape design and can achieve conformal fitting by the reversible collapse of pores. Additionally, the thickness of the individual struts in the architecture and the material it is comprised of can lead to tunable strength and elasticity. Finally, strain can easily be localized by printing these designs with regions of variable porosity or density of material. FIG. 14D illustrates an exemplary use of incorporating tunable Voronoi 3D-printed architectures into mineralized collagen scaffolds for use in bone repair. Mineralized collagen scaffolds offer excellent bioactivity and osteogenic properties due to the mineral, glycosaminoglycans, collagen, and porous nature of this material, however, this porosity also lends to these being very soft structures and more difficult to handle in bone repair situations. 3D-printed Voronoi structures offer a mechanically stable material with tunable mechanics, however, the macro-scale porosity and print material may not be as osteogenic as mineralized collagen scaffolds. Combined together, mineralized collagen and 3D-printed Voronoi structures have the ability to promote osteogenesis while also maintaining strength. Scale bar represents 100 μm.

DETAILED DESCRIPTION

General Considerations

For purposes of this description, certain aspects, advantages, and novel features of examples of this disclosure are described herein. The disclosed methods, compositions, apparatuses, and systems should not be construed as being limiting in any way. Instead, the present disclosure is directed toward all novel and nonobvious features and aspects of the various disclosed examples, alone and in various combinations and sub-combinations with one another. The methods, compositions, apparatuses, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, "e.g." means "for example," and "i.e." means "that is."

Examples of the Disclosed Technology

One method to address mechanical fitting problems (e.g., when repairing irregular bone defects) is through "shape-fitting" designs. Shape-fitting can be achieved through mechanical or chemical means in materials. Chemical modifications of materials have been used in many instances for shape-fitting, such as a biomaterial which can be heated outside the body to allow for surgical shaping to the defect space, and then cooled to body temperature to enable hardening and fit of the implant within the defect. These have been shown to regenerate bone, however, heat treatment of implants may only be possible for specific biomaterial chemical compositions (such as polymers) and may even exclude bio-derived polymers such as collagen, which denature at high temperatures. Alternatively, mechanical methodologies implement design of the structure of implants to be contracted with force by the surgeon, placed within a defect space, and released to fit against the defect. Another strategy has included micro-CT scanning of the patient's defect and 3D-printing implants with uniform pores to fit within this missing space.

Mineralized collagen scaffolds are porous biomaterials comprised of collagen, mineral, and glycosaminoglycans, and have been shown to induce osteogenesis and bone repair without supplemental growth factors or osteogenic media. Although these scaffolds promote bone formation, they are extremely soft with a Young's Modulus on the order of hundreds of kilopascals when dry and tens of kilopascals when hydrated and crosslinked. In comparison, normal human cortical and cancellous bone have Young's Moduli on the order of one to tens of gigapascals. Thus, there remains a need to reinforce these soft scaffolds to promote bone formation while being mechanically robust and flexible to fit well to defect sites.

Provided herein are designs utilizing Voronoi architectures. Voronoi architectures are random, open-porous structures generatable into any size and space by a set of random "seed" points, which make up the center of the pores, or cells, of the Voronoi design (FIG. 2A). The addition of Voronoi structures as tunable reinforcements to soft mineralized collagen scaffolds is disclosed herein. As described below, Voronoi structures with well-defined mechanics based on a predictive equation can be created (for example by 3-D printing), and then implemented within mineralized collagen scaffolds to create a shape-fitting and bone regenerative implant.

I. Composite Materials Utilizing Voronoi Architectures

Provided herein are composite materials that in some examples are suitable for use as implants in repair of bone defects, such as CMF defects. In some embodiments, the composite material includes a macroporous structure (such as a macroporous mesh) having a Voronoi architecture and a biomaterial (such as a microporous biomaterial) associated with or integrated into the macroporous structure.

Embodiments of the disclosed composite materials include a macroporous structure including a plurality of open cells or pores with a Voronoi architecture. A microporous biomaterial is integrated into the macroporous structure. In some embodiments, the macroporous structure is a mesh, for example, including a plurality of pores or open cells. A "macroporous structure" refers in at least some examples to a structure including pores at the μm-mm scale, such as about 10 μm to about 2 mm.

Figure 1A:
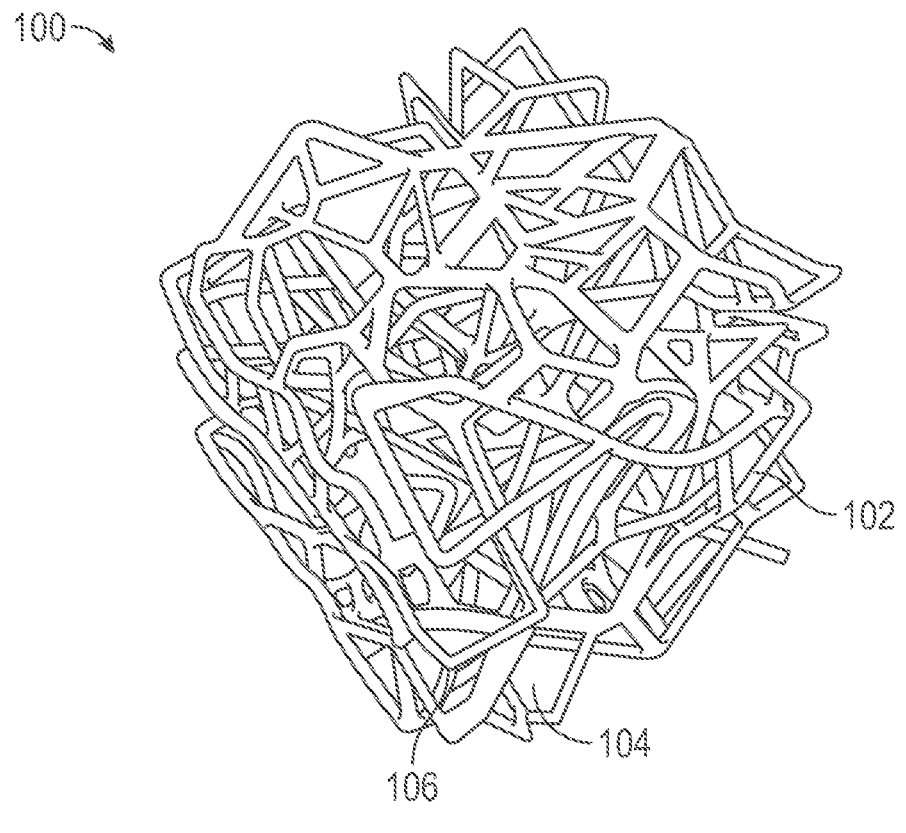
FIG. 1A is a schematic of an exemplary macroporous structure embodiment.

FIG. 1A shows an exemplary macroporous structure 100 that comprises a plurality of fibers 102 (also referred to herein as "struts") that define a plurality of pores 104. The plurality of fibers 102 are connected at connecting points 106 that define a Voronoi architecture. The pores 104 of the macroporous structure may be any shape (such as round, rectangular, square, or polygonal). In some examples, the pores can also be of an irregular shape. In embodiments, each of the plurality of pores have the same shape (or substantially the same shape). In other embodiments, two or more of the plurality of pores in the macroporous structure have different shapes.

In some embodiments, each of the plurality of pores 104 have substantially the same shape and dimensions. In some examples, at least one dimension of the pores 104 (e.g., diameter, length, or width) is at least about 0.5 mm (such as at least about 0.5 mm, at least about 0.6 mm, at least about 0.7 mm, at least about 0.8 mm, at least about 0.9 mm, at least about 1 mm, at least about 1.25 mm, at least about 1.5 mm, at least about 1.75 mm, at least about 2 mm, at least about 2.3 mm, at least about 2.5 mm, at least about 3 mm, at least about 3.5 mm, at least about 4 mm, at least about 4.5 mm, or at least about 5 mm. In other examples, at least one dimension of the pores 104 is about 0.5 mm to about 5 mm, such as about 0.5 mm to about 1.5 mm, about 1 mm to about 2 mm, about 1.5 mm to about 2.5 mm, about 2 mm to about 3 mm, about 2.5 mm to about 3.5 mm, about 3 mm to about 4 mm, about 3.5 mm to about 4.5 mm, or about 4 mm to about 5 mm. In other embodiments, at least one dimension of the pores 104 is less than about 0.5 mm (for example, less than about 0.4 mm, less than about 0.3 mm, less than about 0.2 mm, or less than about 0.1 mm). In other embodiments, the size of the pores is of a size that is sufficient for the biomaterial to enter the pores and be integrated into the macroporous structure.

In some embodiments, the size of pores is defined as the distance between the points, also referred to as "pore spacing" or the distance between each pore from the center of one pore to the center of another. In one example, pore spacing is about 3 mm. In this situation, strut thickness should be taken into account to determine pore size.

In some embodiments, the fibers 102 defining the pores 104 have a diameter of about 10 μm to about 2 mm, such as about 10 μm to about 100 μm, about 50 μm to about 500 μm, about 250 μm to about 750 μm, about 500 μm to about 1 mm, about 750 μm to about 1.25 mm, about 1 mm to about 1.5 mm, about 1.25 mm to about 1.75 mm, or about 1.5 mm to about 2 mm. In some examples, the fibers have a diameter of about 10 μm, 50 μm, 100 μm, 200 μm, 300 μm, 400 μm, 500 μm, 600 μm, 700 μm, 800 μm, 900 μm, 1 mm, 1.1 mm, 1.2 mm, 1.3 mm, 1.4 mm, 1.5 mm, 1.6 mm, 1.7 mm, 1.8 mm, 1.9 mm, or 2 mm. In specific examples, the fiber diameter is about 0.7 mm, about 1 mm, or about 1.5 mm.

Figure 1B:
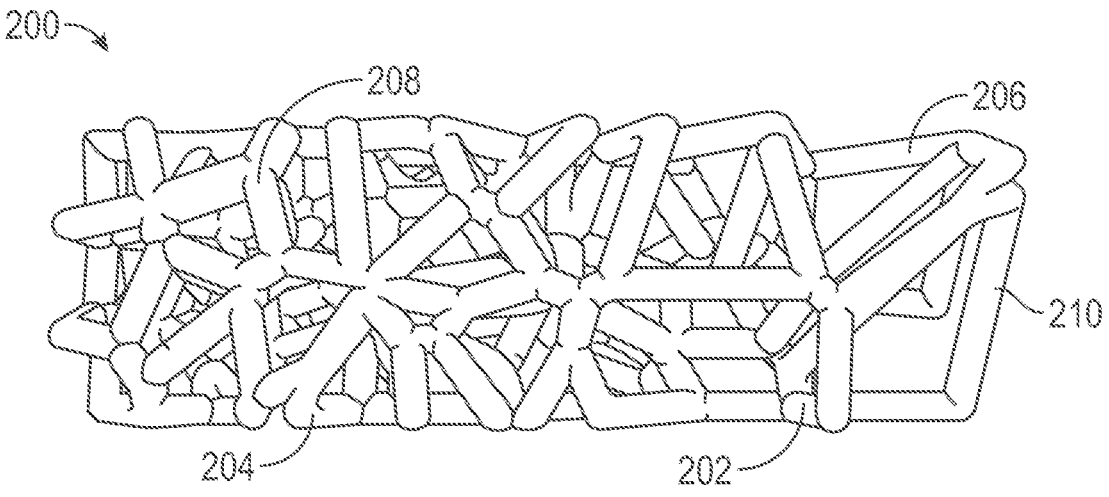
FIG. 1B is a schematic of an exemplary biphasic macroporous structure embodiment.

In other embodiments of the disclosure composite material, the macroporous structure has at least two portions wherein each of the at least two portions have different pore sizes. In some examples, this type of macroporous structure is referred to herein as a "biphasic" structure. FIG. 1B shows an exemplary biphasic macroporous structure 200 including a first portion 202 and a second portion 204. In this embodiment, the pore size 206 of the first portion 202 is larger than the pore size 208 of the second portion. In some embodiments, the ratio of a dimension of the pore 206 of the first portion 202 to a dimension of the pore 208 of the second portion 208 is up to about 10:1 (such as about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1). In one specific example, the ratio is about 1.875:1.

The fibers 210 defining the plurality of pores in the first portion and the second portion of the macroporous structure are of substantially the same size in each portion. In some embodiments, the fibers 102 defining the pores 104 have a diameter of about 10 μm to about 2 mm, such as about 10 μm to about 100 μm, about 50 μm to about 500 μm, about 250 μm to about 750 μm, about 500 μm to about 1 mm, about 750 μm to about 1.25 mm, about 1 mm to about 1.5 mm, about 1.25 mm to about 1.75 mm, or about 1.5 mm to about 2 mm. In some examples, the fibers have a diameter of about 10 μm, 50 μm, 100 μm, 200 μm, 300 μm, 400 μm, 500 μm, 600 μm, 700 μm, 800 μm, 900 μm, 1 mm, 1.1 mm, 1.2 mm, 1.3 mm, 1.4 mm, 1.5 mm, 1.6 mm, 1.7 mm, 1.8 mm, 1.9 mm, or 2 mm. In specific examples, the fiber diameter is about 0.7 mm, about 1 mm, or about 1.5 mm. In some examples, the fiber diameter is substantially the same in the first portion and the second portion. In other examples, the fiber diameter may be different in the first portion and the second portion (for example, about 1:2 or about 2:1).

In other embodiments, the macroporous structure has more than two different portions (such as 3, 4, 5, or more different portions). In such structures, at least one portion has a pore size that is larger than the pore size of at least one other portion of the structure. In some examples, each of the two or more portions have different pore sizes. In examples with three or more portions, each portion may have a different pore size, or at least two portions may have a substantially similar pore size. In certain embodiments, any region can be defined within a shape (say rectangle) and different pore sizes can be set. For example, a rectangle could be broken down into three sections, the ends with one pore size and the middle with another. This similarly could be done with a circle, where a circle is divided into a middle region and an outer region, each with different pore sizes.

In embodiments, the macroporous structure (such as the fibers) are formed from a polymer. Exemplary polymers that can be used to form the macroporous include polycaprolactone (PCL), polylactic acid (PLA), and poly lactic-co-glycolic acid (PLGA). In some examples, the polymer is biocompatible, such as a polymer that performs its desired function without eliciting undesirable local or systemic effects (such as cytotoxicity) in a subject.

In some examples, the amount of polymer in the composite material is an amount that does not elicit undesirable effects in a subject, such as cytotoxicity, inflammation, or an unacceptable level of inflammatory response (such as a persistent inflammatory response). In some examples, the total amount of polymer in the composite material is not more than about 30% (v/v). In other examples, the total amount of the polymer in the composite material is about 5% (v/v) to about 30% (v/v), such as about 5% (v/v) to about 15% (v/v), about 10% (v/v) to about 20% (v/v), about 15% (v/v) to about 25% (v/v), or about 20% (v/v) to about 30% (v/v). In other examples, the total amount of polymer in the composite material is about 5% (v/v), about 10% (v/v), about 15% (v/v), about 20% (v/v), about 25% (v/v), about 30% (v/v), about 6-8% (v/v), about 10-12% (v/v), or about 18-20% (v/v).

In some embodiments, the macroporous structure (and the resulting composite material) is a two-dimensional (or substantially two-dimensional) structure. An exemplary macroporous structure in the form of a two-dimensional sheet is illustrated in FIG. 12A. In such examples, the two-dimensional structure has a first surface (such as a top surface) and a second surface (such as a bottom surface). In other embodiments, the macroporous structure (and the resulting composite material) is a three-dimensional structure. The three-dimensional structure can be any shape, including a three-dimensional sheet (for example, as illustrated in FIG. 12A), a cube or substantially cubical (for example, as illustrated in FIG. 1A), a rectangular or substantially rectangular structure (for example, as illustrated in FIG. 1B), or a cylindrical or substantially cylindrical structure. The three-dimensional structure can also be of an irregular shape, such as a shape to conform to a bone defect in a subject.

The disclosed macroporous structures (and the resulting composite materials) can be of any size. In some examples, the macroporous structure is the size of a bone defect. In some examples, the macroporous structure is at least about 20 mm in at least one dimension, such as at least about 20-100 mm in at least one dimension, for example at least about 20 mm, at least about 25 mm, at least about 30 mm, at least about 35 mm, at least about 40 mm, 45 mm, at least about 50 mm, or more in at least one dimension. In other examples, the macroporous structure is a larger and/or non-specific size, which can be cut and shaped to the desired size and shape for treating a subject with a bone defect.

In some embodiments, the macroporous structure is isotropic, for example, having the same properties in all axes. In other embodiments, the macroporous structure is anisotropic, for example, having different properties in at least one axis compared to at least one other axis. Material anisotropy may arise intentionally (for example, by stretching the Voronoi mesh in one axes to induce structural alignment) or may be due to the material design (e.g., planar materials where one direction (such as thickness) is comprised of only a few pores).

The stiffness of the disclosed composite materials can be tuned based on the density of the pores in the macroporous structure. For example, a macroporous structure with a higher density of pores (for example, smaller pores defined by more closely placed connecting points of the fibers) will have higher stiffness or lower deformability. A macroporous structure with a lower density of pores (for example, larger pores defined by more distantly placed connecting points of the fibers) will have lower stiffness or higher deformability. In some embodiments, the Young's modulus of the macroporous structure is between about 100 kPa and about 250 MPa, for example from about 100 kPa to about 500 kPa, about 250 kPa to about 750 kPa, about 500 kPa to about 1 MPa, about 1 MPa to about 5 MPa, about 2.5 MPa to about 10 MPa, about 7.5 MPa to about 15 MPa, about 10 MPa to about 20 MPa, about 15 MPa to about 40 MPa, about 25 MPa to about 50 MPa, about 30 MPa to about 75 MPa, about 50 MPa to about 100 MPa, about 100 MPa to about 150 MPa, about 125 MPa to about 175 MPa, about 150 MPa to about 200 MPa, about 175 MPa to about 225 MPa, or about 200 MPa to about 250 MPa. In one embodiment of a biphasic material, a "porous" region could have a Young's modulus of about 1-5 MPa and a "dense" region could have a Young's modulus of about 10-40 MPa.

In additional embodiments, the macroporous structure is capable of elastic deformation for up to 20% of applied strain, such as up to 5%, up to 10%, up to 15%, or up to 20% of applied strain. Elastic deformation refers to reversible or temporary deformation. In other embodiments, the macroporous structure is capable of plastic deformation for up to 80% of applied strain, such as up to 5%, up to 10%, up to 15%, up to 20%, up to 25%, up to 30%, up to 35%, up to 40%, up to 45%, up to 50%, up to 55%, up to 60%, up to 65%, up to 70%, up to 75%, or up to 80% of applied strain. Plastic deformation refers to permanent or non-reversible deformation.

Figures 6A, 6B, 6C:
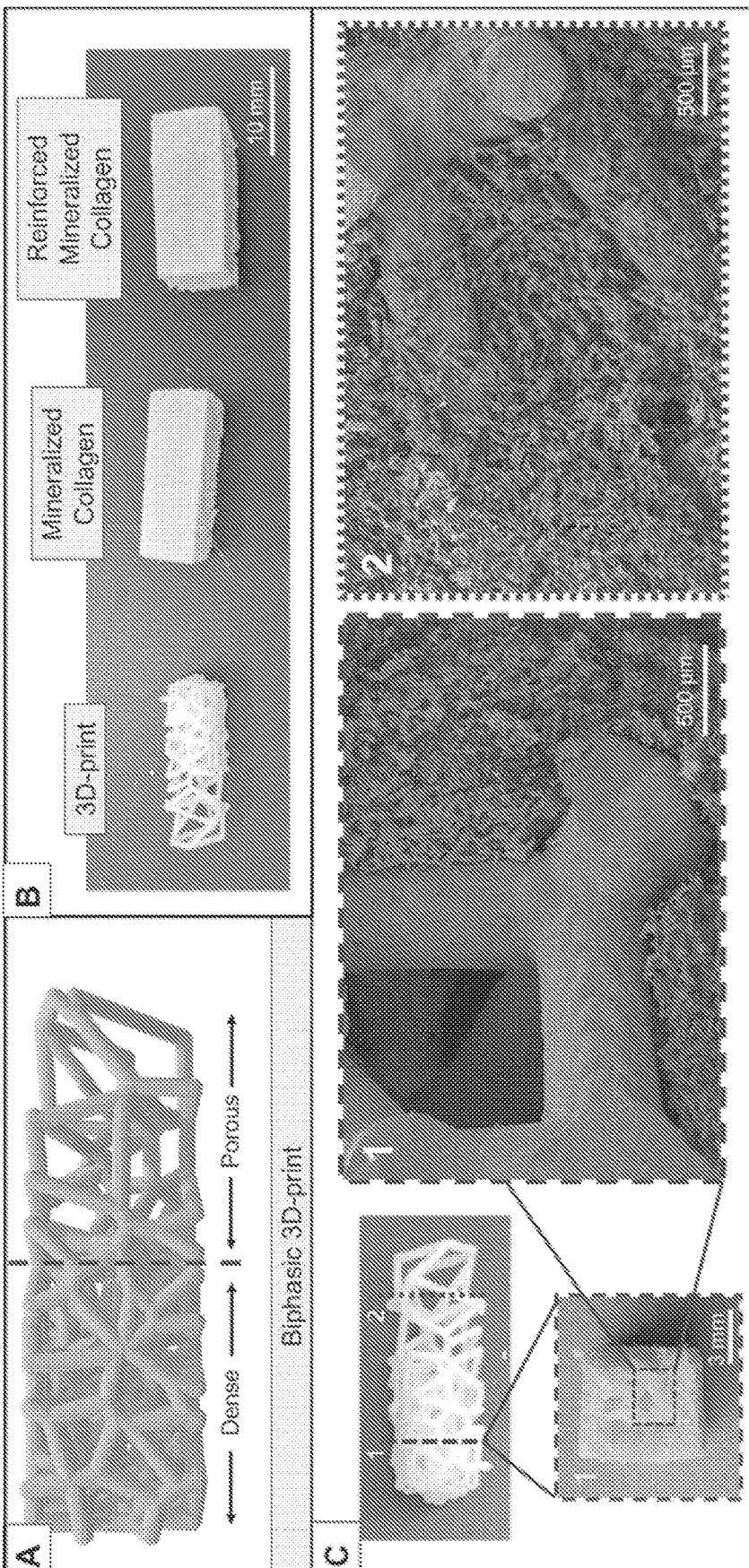
FIGS. 6A-6C illustrates the structure of mineralized collagen scaffolds reinforced with a biphasic Voronoi 3D-print.

The disclosed composite materials include a microporous biomaterial that is integrated into or associated with the macroporous structure. A "microporous biomaterial" refers to a structure including pores at the nm-µm scale, such as about 100 nm to about 10 µm. In some examples, the biomaterial is not covalently linked to the macroporous structure. In other embodiments, the biomaterial is covalently linked to the macroporous structure, for example by a linker. In one example, covalent linkage includes crosslinking of collagen fibers to the support structure, such as using EDC-NHS chemistry or other chemicals which can covalently link the end groups of collagen to the end groups of the 3D-printed materials. In some embodiments, the biomaterial substantially fills all of the porous space in the macroporous structure (see, e.g., FIG. 6C, part 2). In other embodiments, the biomaterial does not completely fill all of the porous space in the macroporous structure (see, e.g., FIG. 6C, part 1).

In some embodiments, the biomaterial includes one or more components that are biocompatible and are suitable for use in repair of a bone defect. In some examples, the biomaterial includes collagen, glycosaminoglycans, calcium phosphate, or a combination of two or more thereof. In one example, the biomaterial is mineralized collagen, for example, produced by combining collagen with calcium phosphate during fabrication of the composite (see Section II, below). In some examples, the biomaterial includes other extracellular matrix materials (which contain collagen), and may also include minerals, glycosaminoglycans, and other chemicals or additives (honey, growth factors, proteins, etc.).

II. Methods of Making the Composite Materials

Methods of making the disclosed composite materials are provided herein. In some embodiments, the methods include contacting a macroporous structure (such as that described in Section I) with a solution including a liquid suspension of a biomaterial. The liquid is them removed from the solution in contact with the macroporous structure, producing the composite material.

In some embodiments, contacting the macroporous structure with the solution includes submerging the macroporous structure in the solution. The liquid can be removed by cooling the macroporous structure and solution to a temperature at which the liquid transforms into a plurality of solid crystals and removing at least some (or substantially all) of the crystals by sublimation or evaporation. In some examples, the liquid is removed by lyophilization. In one example, the suspension is lyophilized by reducing the temperature to about −10° C. at a rate of about 1° C./minute and holding at −10° C. for a sufficient period of time for sublimation of the crystals, for example about 2 hours. The resulting composite material is brought back to room temperature and atmospheric pressure. In some examples, the pressure is released and temperature is increased rapidly, for example over about 2-3 minutes.

In other embodiments, other lyophilization conditions include altering the hold temperature (−40° C., −60° C., etc.), altering the rate of freezing (for example, slower (such as 1° C./2 min) or faster (such as 5° C./min), which can result in different pore architectures of the resulting material.

In some embodiments, the solution includes a liquid suspension of collagen (for example, about 2% w/v collagen). In some examples, the collagen is type I collagen. The collagen may be human type I collagen, bovine type I collagen, or xenografts (such as porcine dermis, for example for wound healing). The solution may also contain calcium and phosphorus, for example, for producing mineralized collagen. In some examples, the solution includes about 2% w/v type I collagen, about 40% w/v mineral solution of phosphoric acid and calcium hydroxide. Additional components that can be added to the solution include zinc (see, e.g., Tiffany et al., *Acta Biomaterialia* 93:86-92, 2019), growth factors (such as BMP2, see e.g., Tiffany et al., *RSC Advances* 10:26982, 2020), glycosaminoglycans, such as chondroitin (for example, 0.5-1% v/v chondroitin sulfate sodium salt), heparin or heparan sulfate, dermatan sulfate, keratan sulfate, hyaluronic acid, or amniotic membrane from placenta (see, e.g., Kolliopoulos et al., *Frontiers in Bioengineering and Biotechnology* 10:1034701, 2022). Calcium nitrate tetrahydrate can also be added.

The methods also include preparing the macroporous structure in some embodiments. The macroporous structure can be produced by any suitable method, including additive manufacturing (e.g., 3D printing) methods or laser sintering. In some examples, the methods also include designing a Voronoi structure with the desired characteristics, for example by selecting the distance between the connecting points of the fibers defining the pores or the macroporous structure ("point spacing") and the diameter of the fibers. The design can be carried out using commercially available software packages, such as nTop software (nTopology, New York) or Fusion360 software (Autodesk, California). In some examples, a generative design process is used to produce a Voronoi architecture of random shape. For example, a program may allow for the user to set a point-spacing of Voronoi design across a user-set print size, such as a rectangle, and the program will design the Voronoi outline to fill this space. The user can then select the strut thickness of the print. The macroporous structure can be produced from a design by additive manufacturing, such as extrusion printing (e.g., fused deposition modeling). In some examples, standard 3D-printing, photolithograph/stereo-lithography, and/or laser sintering can be used to produce the macroporous structure.

In some embodiments, the composite material can be sterilized. Once produced, the composite material can be stored until ready to use. In some examples, the composite material is stored in a desiccator at room temperature. When ready to use, the composite material can be rehydrated, for example, by soaking in a sterile solution, such as saline, Ringer's solution, or another physiologically suitable fluid. In some examples, the solution may include one or more biomolecules, such as one or more growth factors (e.g., BMP2 or VEGF), honey, or antibiotics.

III. Methods of Treating Bone Defects

The composite materials described herein may be used to treat a bone defect in a subject. In embodiments, the methods include implanting a disclosed composite material in, or at the site of, a bone defect in a subject. The composite material is surgically implanted at the site of a bone defect in order to treat the bone defect. In some examples, the material is fastened in place (such as with a fastener or adhesive). In other examples, the material is conformally fitted and does not require fastening. The subject may be a human or animal subject (such as a laboratory animal, companion animal, or livestock).

In some embodiments, the composite material is sized to fit the defect to be repaired. In other embodiments, the methods include shaping the composite material to the bone defect prior to implanting in the subject. In some examples, a composite material (such as a previously produced composite material) is trimmed to the size and shape of the bone defect in the subject. In other examples, a composite material is deigned specifically to fit the bone defect of a subject and is produced using the methods described herein. In the case of a composite material specifically designed to fit a subject's bone defect, some trimming and/or shaping may be needed prior to implanting to improve the fit of the composite in the defect. In additional embodiments, a two-dimensional or three-dimensional composite material may be used for treating a bone defect, depending on the location or type of defect. For example, a two-dimensional composite material may be used to treat a defect of the eye orbital or a cranial defect, while a three-dimensional composite material may be used to treat a defect of the jaw.

In some embodiments, the composite material deforms to fit the defect. In particular examples, the composite material includes a biphasic macroporous structure such that it includes a region of capable of high deformation, which improves conformal fitting (for example at one or more edges of the structure) and a region of little or no deformation, which provides increased mechanical support and stability due to increased stiffness (for example in a central region of the structure).

In additional embodiments, the methods of treating a bone defect include hydrating a previously produced composite material in a sterile solution prior to implanting the composite in the bone defect in the subject. In other embodiments, the methods further include designing and producing a composite material having characteristics (such as Voronoi architecture, size, and shape) selected for the particular bone defect to be treated.

In some embodiments, a bone defect includes a disease, defect, or disorder which affects bone strength, function, and/or integrity, such as those resulting from injury or trauma, or a defect brought about during the course of surgery, infection, malignancy, or developmental malformation. Examples of bone defects include, but are not limited to, fractures (such as a critical defect or non-union fracture) and craniomaxillofacial defects (such as cleft palate or facial or dental injuries or malformations), non-union fractures, or for treatment of any portion of missing bone (such as bone removed by resection, such as for osteosarcoma). In some embodiments, the bone defect is a defect, fracture, or injury of one or more cranial bones, such as the frontal bone, parietal bone, temporal bone, occipital bone, sphenoid bone, or ethmoid bone or one or more facial bones, such as the zygomatic bone, superior and inferior maxilla, nasal bone, mandible, palantine bone, lacrimal bone, vomer bone, or the inferior nasal conchac.

Additional Examples of the Disclosed Technology

The following examples are provided to illustrate certain particular features and/or embodiments. These examples should not be construed to limit the disclosure to the particular features or embodiments described.

Example 1

Materials and Methods

Three objectives were pursued in these studies (FIG. 2B): (1) Alter the thickness and porosity of Voronoi designs to determine how changes in this relate to a predictive equation and stiffness changes and examine isotropy to determine if the direction of force applied on these designs results in different stiffnesses; (2) Create biphasic Voronoi structures to determine if stiffness and strain can be localized to one region and how these integrate with mineralized collagen scaffolds; and (3) Test the shape-fitting ability of 2D and 3D Voronoi "sheets" and how these integrate with mineralized collagen scaffolds and how these can be cut and trimmed to shape.

Fabrication of 3D-printed Voronoi structures: All 3D Voronoi structures were designed using nTop software (nTopology, New York, USA) and 2D designs were designed using Fusion360 (Autodesk, California, USA). Point spacing was defined as the distance (mm) between the randomly seeded points within a Voronoi structure.

Fabrication of photopolymerized Voronoi structures: Voronoi structures made of photopolymerized resin were created for two different objectives, 1 and 2. Objective 1 structures measured 10 mm cubes with three different porosities and were created by altering the Voronoi point spacing (4 mm point spacing, 3.5 mm point spacing, 3 mm point spacing) with 0.7 mm strut diameter. The porosity was further minimized by printing 0.5 mm strut diameter prints with 4 mm point spacing. These .stl files were added to a Form 2 photopolymerization printer (Formlabs, Massachusetts, USA). A white standard resin and a Dental SG resin (Formlabs) were used to create all samples for objective 1. Dental resin was cured post-print with a Form Cure (Formlabs). Objective 2 structures were made of white resin, and these designs were fabricated as 20×6×6 mm (length, width, height) Voronoi rectangular prints with a point spacing of 2 on one half of the structure and a point spacing of 3.75 on the other half, and printed with a strut thickness of 0.7 mm diameter. These were compared to uniform Voronoi rectangles, measuring the same dimensions and a point space of 2 throughout the space.

Fabrication of laser-sintered Voronoi structures: Voronoi structures used for objective 1 and 3 were created by laser sintering poly (caprolactone). The Voronoi structures were manufactured using laser sintering with an EOS Formiga P110. These structures were fabricated using a blend of polycaprolactone (PCL), a bioresorbable and biodegradable polyester, with a 4% weight by weight ratio of hydroxyapatite, a naturally occurring mineral. Voronoi structures for objective 1 were fabricated as 25 mm cubes with the same pore spacing (3 mm) and various strut thicknesses (0.7 mm, 1 mm, 1.5 mm). Voronoi structures for objective 3 were fabricated as either 2D or 3D sheets, with 2D sheets measuring 74×74 mm squares with 245 cells and 80% cell scale, and 3D sheets measuring 74×74×6 mm (length, width, height) and 3 point spacing and 0.7 mm strut thickness.

Fabrication of Voronoi-mineralized collagen composite structures: Voronoi-mineralized collagen composites were fabricated for objectives 2 and 3. Mineralized collagen suspension was created and composites were fabricated via lyophilization. Briefly, 1.9 w/v % type I bovine collagen (Collagen Matrix, New Jersey, USA or Sigma Aldrich, Missouri, USA) was blended together with a 40 wt % mineral solution of phosphoric acid (Fisher Scientific, New Hampshire, USA) and calcium hydroxide (Sigma Aldrich), 0.84 v % chondroitin sulfate sodium salt (CAS 9082-07-9, Spectrum Chemicals, New Jersey, USA), and calcium nitrate tetrahydrate (Sigma Aldrich) using a rotor-stator in a jacketed cooling vessel until well-blended. To create mineralized collagen scaffolds, 24 mL or 48 mL of suspension (for 3.5 mm or 7.5 mm thickness sheets, respectively) was pipetted into a 75×75 mm aluminum pan. To create biphasic or uniform Voronoi-mineralized collagen composites for objective 2, 48 mL of suspension was added to a 75×75 mm aluminum pan and individual rectangular 3D-prints were carefully added to pan, making sure to cover the print with suspension. To create Voronoi-mineralized collagen composite sheets for objective 3, 24 mL or 48 mL of suspension (for 2D or 3D composites, respectively) was pipetted into a 75×75 mm aluminum pan and Voronoi 3D-printed structures were carefully added to this with tweezers, making sure to cover the 3D-prints with the suspension. The suspensions were then lyophilized using a Genesis freeze-dryer (VirTis, New York, USA) by dropping the temperature at a rate of 1° C./min to −10° C., then holding these at −10° C. for 2 hours, and then these were brought back to room temperature and atmospheric pressure. Resulting mineralized collagen and composites were in the form of solid sheets. For objective 2, composites were removed by a razor blade. For objective 3, composites were removed with 12 mm biopsy punches.

Predictive equation for Voronoi structures: A predictive modulus equation for open-cell foams was used to predict the Elastic Modulus of Voronoi structures.

$$\frac{E^*}{E_s} = \left(\frac{\rho^*}{\rho_s}\right)^2$$

Where E* represents the Predictive Young's Modulus, $E_s$ represents the Young's Modulus of the solid skeleton, and (p*/p$_s$) represents the reduced density. The predictive modulus values were determined by calculating the v/v % of Voronoi designs based on .stl files (known densities) and normalizing these to the design with the greatest volume of 3D-print (i.e. thickest or most dense print). Thus the Voronoi architecture with the highest relative density was the "base" (value of 1) design, and was used to calculate the expected modulus of the remaining Voronoi architectures with smaller relative densities based on the known differences in relative density.

Compression testing of Voronoi structures: All Voronoi structures created underwent compression testing and were analyzed with a custom Matlab program in order to determine Young's Modulus, Ultimate Stress, and Ultimate Strain as open porous foam structures. All structures were loaded onto platens facing the same direction (same face upward). To test isotropy, each design was tested on each face of the cube (x, y, z axis). Matching experimental data to a predictive equation was determined by normalizing the other designs tested to the design with the highest density of 3D-print.

Compression of Voronoi structures for objective 1: Photopolymerized resin Voronoi structures printed as 10 mm cubes were mechanically compressed by an Instron 5943 mechanical tester (Instron, Massachusetts, USA). A 100 N load cell was used at a rate of 1 mm/min to generate data for stress-strain curves. Six samples were used for each design and each face tested for 10 mm cube designs. Laser-sintered polycaprolactone Voronoi structures printed as 25 mm cubes were mechanically loaded and unloaded to half the thickness of the print. A MTS Criterion model 43 (MTS, Minnesota, USA) was used to compress at a rate of 1 mm/sec with a 1 kN load cell and holding at 1 sec before releasing at a rate of 1 mm/sec. Videos of prints were taken using a Pixelink camera (Pixelink, Canada). Only the 0.7 mm thickness print was used to test for isotropy. Percent deformation of samples was determined by the difference in the strain after unloading compared to the strain at the start of the experiment. Eight samples were used for each thickness and face tested for 25 mm cube designs.

Compression and DIC testing of Voronoi structures for objective 2: Biphasic Voronoi structures were compressed by an Instron 5943 mechanical tester (Instron) with a 100 N load cell at a rate of 3 mm/min to generate data for stress-strain curves. 3D-printed Voronoi-mineralized collagen composites were tested with a biphasic 3D-print and a uniform 3D-print (n=6). Rectangular scaffolds were glued to 3D-printed bases (ABS) to stabilize these to the mechanical platens, with the dense region of the biphasic structure always glued to the base. Following embedding into the ABS base, scaffolds were speckle-patterned with waterproof India ink (BLICK Art Materials, Illinois, USA) using a gravity feed airbrush with a nozzle size of 0.3 mm (Got Hobby Inc., California, USA). During uniaxial compression testing, images were taken with a Canon EOS 5DS R DLSR camera and a Canon Macro 100-mm lens at a rate of 1 image every 5 seconds until an arbitrary point of maximum compression (Canon, Tokyo, Japan). The digital images were correlated. Briefly, the sets of images taken during compression testing were correlated using a version of the MATLAB file package "Digital Image Correlation and Tracking" (Copyright 2010, C. Eberl, D. S. Gianola, S. Bundschuh) modified by Elizabeth Jones (Improved Digital Image Correlation version 4-Copyright @ 2013, 2014, 2015 by Elizabeth Jones) to calculate local strain across scaffolds. For each set of scaffold images, the region of interest was set as the entire exposed scaffold and full images were correlated (subset size: 221-421; threshold 0.5; search zone: 2; grid step size: 25). Finally, displacements were smoothed prior to calculating strains to reduce noise (Gaussian distribution of weights; kernel size: 11; number of smoothing passes: 3; maximum size of contiguous non-correlated points to smooth over: 15) and local strains were calculated using a cubic (16-node) algorithm. Due to high displacements, images near the maximum compression did not correlate. Therefore, strain profiles were analyzed from the start of compression to simply show the localization of strain throughout the scaffold in biphasic versus uniform Voronoi structures. Scaffolds without any 3D-print, biphasic Voronoi-mineralized collagen composites, and uniform Voronoi-mineralized collagen composites were tested to analyze elastic modulus regimes from stress-strain curves using the same mechanical tester, a 100 N load cell at a compression rate of 3 mm/min.

Push-out testing of Voronoi structures and composites for objective 3: 2D and 3D Voronoi-mineralized collagen sheets underwent push-out testing to determine shape-fitting ability compared to mineralized collagen scaffolds without printed supports. 12 mm biopsy punches were used to remove samples from sheets, and these were added to two defect sizes in a Teflon mold, either 11.5 mm or 10.8 mm in diameter. The Teflon mold was applied to an apparatus allowing for a metal pin to push the composites or scaffolds through the defects. The maximum push out force (N) was measured and compared between groups, with eight samples per group. 2D Voronoi composites were compared to mineralized collagen scaffolds of the same thickness (approximately 3.5 mm thick) and 3D Voronoi composites were compared to mineralized collagen scaffolds of the same thickness (approximately 7.5 mm thick).

SEM imaging of Voronoi and mineralized collagen composites: The 3D-print integration with mineralized collagen scaffolds was visualized via SEM of photopolymerized biphasic Voronoi-mineralized collagen composites, and 2D and 3D Voronoi-mineralized collagen composites. Biphasic composites were cut in both phases to expose the interior of the dense and porous regions, and 2D and 3D Voronoi composites were cut in half to visualize the center of these composites.

Statistics: Data were first checked for normality (Shapiro-Wilk) and equal variance (Levene's Test) of residuals, using a Grubb's test to check for and remove any outliers. If data were normal with equal variance, a One-way ANOVA was used with a Tukey post-hoc to determine significance ($p < 0.05$) between more than 2 groups. For only two group comparisons, a two sample T-test was used, and data was marked only significant if the power was above 0.8.

Example 2

Analysis of Young's Modulus and Isotropy

Figure 3A:
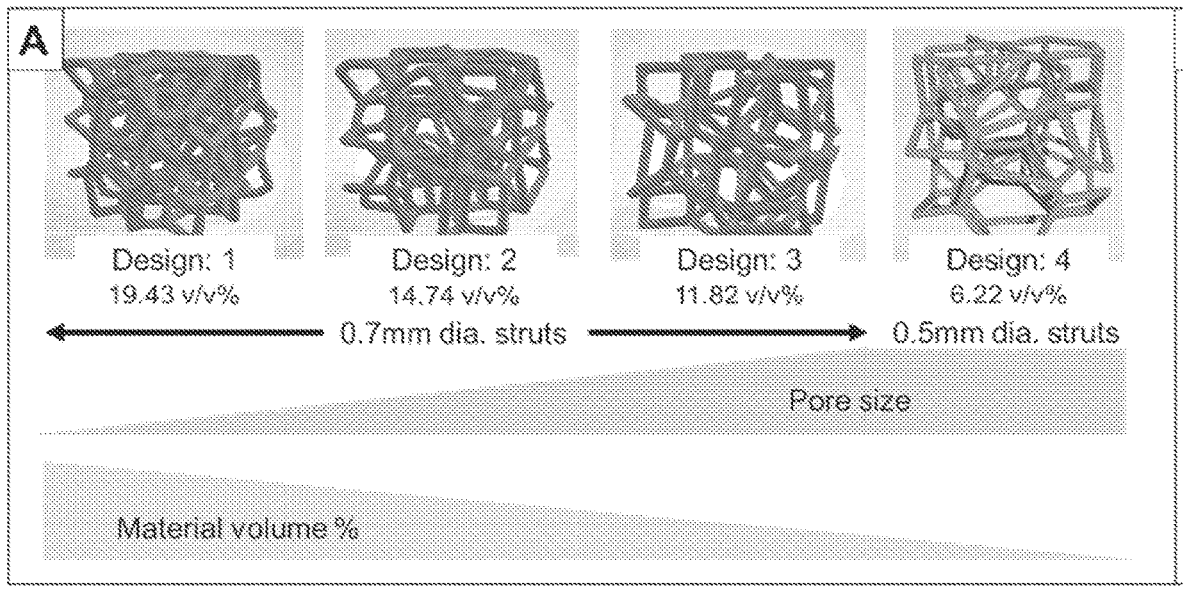
FIGS. 3A and 3B show relationship of changes in porosity of small Voronoi cubes to a predictive modulus equation.
Figure 3B:
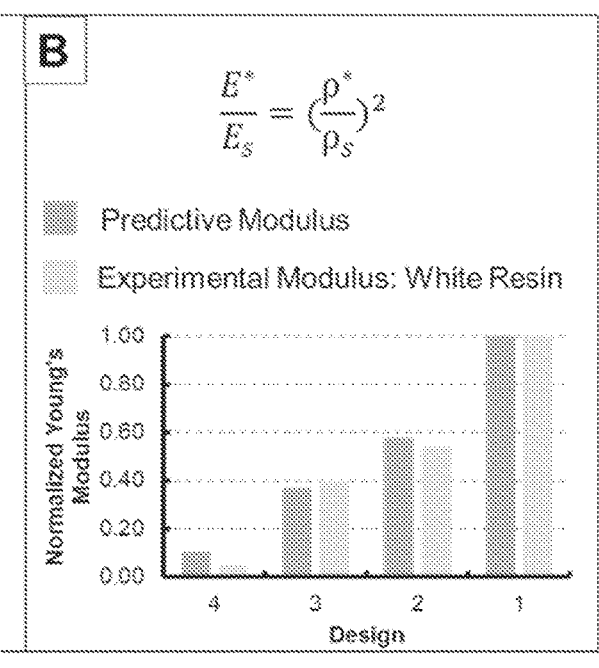

Four different porosity Voronoi structures were tested for stiffness (19.43 v/v %, 14.74 v/v %, 11.82 v/v %, 6.2 v/v %). The Young's Moduli of these four different porosities of Voronoi designs was evaluated with prints of either white or dental photopolymerized resin. Overall, the Young's Moduli of 0.7 mm strut diameter Dental resin 3D prints were greater than those of the white print (Table 1). Denser Voronoi structures also led to higher Young's Moduli, and if printed with white photopolymerized resin, these matched a predictive modulus closely (FIG. 3B, Table 2).

TABLE 1

Comparison of the Young's modulus of different porosity Voronoi 3D-prints made of white or dental resin.

| Sample | Side | Dental Resin Young's Modulus (MPa) | White Resin Young's Modulus (MPa) |
|---|---|---|---|
| 0.5 mm dia 4 pore | 1 | 0.19 ± 0.13 | 0.13 ± 0.05 |
| | 2 | 0.38 ± 0.09 | 0.18 ± 0.04 |
| | 3 | 0.14 ± 0.13 | 0.09 ± 0.07 |
| 0.7 mm dia 4 pore | 1 | 4.12 ± 0.91 | 1.98 ± 0.16 |
| | 2 | 12.4 ± 1.92 | 1.35 ± 0.17 |
| | 3 | 8.94 ± 0.96 | 1.00 ± 0.18 |
| 0.7 mm dia 3.5 pore | 1 | 5.91 ± 2.76 | 2.35 ± 0.26 |
| | 2 | 7.00 ± 2.80 | 2.39 ± 0.16 |
| | 3 | 10.5 ± 2.27 | 1.65 ± 0.23 |
| 0.7 mm dia 3 pore | 1 | 11.6 ± 3.10 | 4.35 ± 0.07 |
| | 2 | 11.4 ± 1.77 | 3.49 ± 0.44 |
| | 3 | 9.02 ± 0.77 | 2.51 ± 0.33 |

TABLE 2

Determination of predictive modulus and experimental modulus of Voronoi 3D prints made of either white or Dental resin based on point spacing and strut thickness.

| | | | | | Experimental data (dental resin) | | Experimental Data (white resin) | |
|---|---|---|---|---|---|---|---|---|
| | Predictive Equation | | | | Young's | | Young's | |
| Design | v/v % | $\rho^*/\rho_s$ | $(\rho^*/\rho_s)^2$ | Normalized E* | Modulus (MPa) | Normalized E* | Modulus (MPa) | Normalized E* |
| 4 | 6.22 | 0.06 | 0.004 | 0.11 | 0.14 | 0.01 | 0.17 | 0.05 |
| 3 | 11.82 | 0.12 | 0.014 | 0.37 | 8.48 | 0.80 | 1.42 | 0.40 |
| 2 | 14.74 | 0.15 | 0.022 | 0.58 | 7.82 | 0.73 | 1.93 | 0.54 |
| 1 | 19.43 | 0.19 | 0.038 | 1.00 | 10.66 | 1.00 | 3.57 | 1.00 |

The Young's Moduli of three different thicknesses (0.7 mm, 1 mm, 1.5 mm) of Voronoi designs printed with laser-sintered polycaprolactone were compared. The Young's Modulus of each thickness was significantly (p<0.05) different from one another, with the 1.5 mm, 1 mm, and 0.7 mm thicknesses having an average of 20.64 MPa, 5.86 MPa, and 1.02 MPa, respectively (Table 3, FIG. 4). When compared to the predictive modulus of these designs, the experimental values closely matched (FIG. 4, Table 4). Compression and release of samples to determine deformation demonstrated that with an increase in thickness, there was an increase in deformation without recovery (Table 5, FIG. 5B). Additionally, videos of compressive loading and unloading of 3D-prints demonstrated the flexibility of prints, with the 0.7 mm strut thickness print showing buckling behavior (not shown).

TABLE 3

Comparison of Young's modulus, ultimate stress and strain, and % deformation after loading of 25 mm dia. Voronoi cubes printed of PCL in three different diameter struts (0.7, 1, and 1.5 mm, Objective 1). Additionally, the 0.7 mm cube design was compressed on each of its 3 faces (x, y, z) to determine changes in these properties.

| Sample | Young's Modulus (MPa) | Ultimate Stress (MPa) | Ultimate Strain (mm/mm) | Deformation after Loading ( %) |
|---|---|---|---|---|
| Side 1 | 0.74 ± 0.05 | 0.04 ± 0.003 | 0.07 ± 0.006 | 2.95 ± 0.69 |
| Side 2 | 1.02 ± 0.05 | 0.05 ± 0.003 | 0.09 ± 0.004 | 3.97 ± 0.23 |
| Side 3 | 1.01 ± 0.06 | 0.05 ± 0.004 | 0.09 ± 0.002 | 3.61 ± 0.41 |
| 0.7 mm | 1.02 ± 0.05 | 0.05 ± 0.003 | 0.09 ± 0.004 | 3.97 ± 0.23 |
| 1.0 mm | 5.86 ± 0.36 | 0.31 ± 0.01 | 0.10 ± 0.002 | 5.58 ± 0.68 |
| 1.5 mm | 20.64 ± 1.23 | 1.15 ± 0.07 | 0.12 ± 0.002 | 10.57 ± 0.18 |

TABLE 4

Determination of predictive modulus and experimental modulus of Voronoi 3D prints made of polycaprolactone based on strut thickness.

| Design (mm) | v/v % | $\rho^*/\rho_s$ | $(\rho^*/\rho_s)^2$ | Normalized E* | Modulus (MPa) | Normalized E* |
|---|---|---|---|---|---|---|
| | | Predictive Equation | | | Experimental Data — Young's | |
| 0.7 | 7.72 | 0.08 | 0.01 | 0.06 | 1.02 | 0.05 |
| 1 | 14.47 | 0.14 | 0.02 | 0.22 | 5.86 | 0.28 |
| 1.5 | 30.96 | 0.31 | 0.10 | 1.00 | 20.64 | 1.00 |

TABLE 5

Comparison of Young's modulus, ultimate stress and strain, and % deformation after loading of 25 mm dia. Voronoi cubes printed of PCL in three different diameter struts (0.7, 1, and 1.5 mm, Objective 1). Additionally, the 0.7 mm cube design was compressed on each of its 3 faces (x, y, z) to determine changes in these properties.

| Sample | Young's Modulus (MPa) | Ultimate Stress (MPa) | Ultimate Strain (mm/mm) | Deformation after Loading (%) |
|---|---|---|---|---|
| Side 1 | 0.74 ± 0.05 | 0.04 ± 0.003 | 0.07 ± 0.006 | 2.95 ± 0.69 |
| Side 2 | 1.02 ± 0.05 | 0.05 ± 0.003 | 0.09 ± 0.004 | 3.97 ± 0.23 |
| Side 3 | 1.01 ± 0.06 | 0.05 ± 0.004 | 0.09 ± 0.002 | 3.61 ± 0.41 |
| 0.7 mm | 1.02 ± 0.05 | 0.05 ± 0.003 | 0.09 ± 0.004 | 3.97 ± 0.23 |
| 1.0 mm | 5.86 ± 0.36 | 0.31 ± 0.01 | 0.10 ± 0.002 | 5.58 ± 0.68 |
| 1.5 mm | 20.64 ± 1.23 | 1.15 ± 0.07 | 0.12 ± 0.002 | 10.57 ± 0.18 |

Isotropy of various Voronoi designs was investigated by compressing the three faces (x, y, z axis) of resin and polycaprolactone 3D-prints. Both Dental and white resin prints demonstrated anisotropy regardless of print porosity or thickness (Table 6). Compression of the 0.7 mm thickness polycaprolactone 3D print also demonstrated anisotropy, as the Young's Modulus and amount of deformation was dependent on what side was compressed (FIGS. 7A and 7B).

TABLE 6

Comparison of significance between Young's Modulus of various sides tested of white and Dental resins.

| Design | Side | Dental Resin 1 | 2 | 3 | White Resin 1 | 2 | 3 |
|---|---|---|---|---|---|---|---|
| 0.5 mm dia. | 1 | | * | x | | x | x |
| 4 pore | 2 | * | | * | x | | x |
| | 3 | x | * | | | x | x |
| 0.7 mm dia. | 1 | | x | x | | * | * |
| 4 pore | 2 | x | | * | * | | * |
| | 3 | x | * | | * | * | |
| 0.7 mm dia. | 1 | | x | * | | x | * |
| 3.5 pore | 2 | x | | x | x | | * |
| | 3 | * | x | | * | * | |
| 0.7 mm dia. | 1 | | x | x | | * | * |
| 3 pore | 2 | x | | * | * | | x |
| | 3 | x | * | | * | x | | x represents the sides are not significantly (p < 0.05) different from one another.
* represents the sides are significantly (p < 0.05) different from one another.

Example 3

Biphasic Voronoi Structures

Figures 8A, 8B:
FIGS. 8A and 8B show mechanics of mineralized collagen scaffolds reinforced with a biphasic Voronoi 3D-print.
Figures 9A, 9B, 9C, 9D:
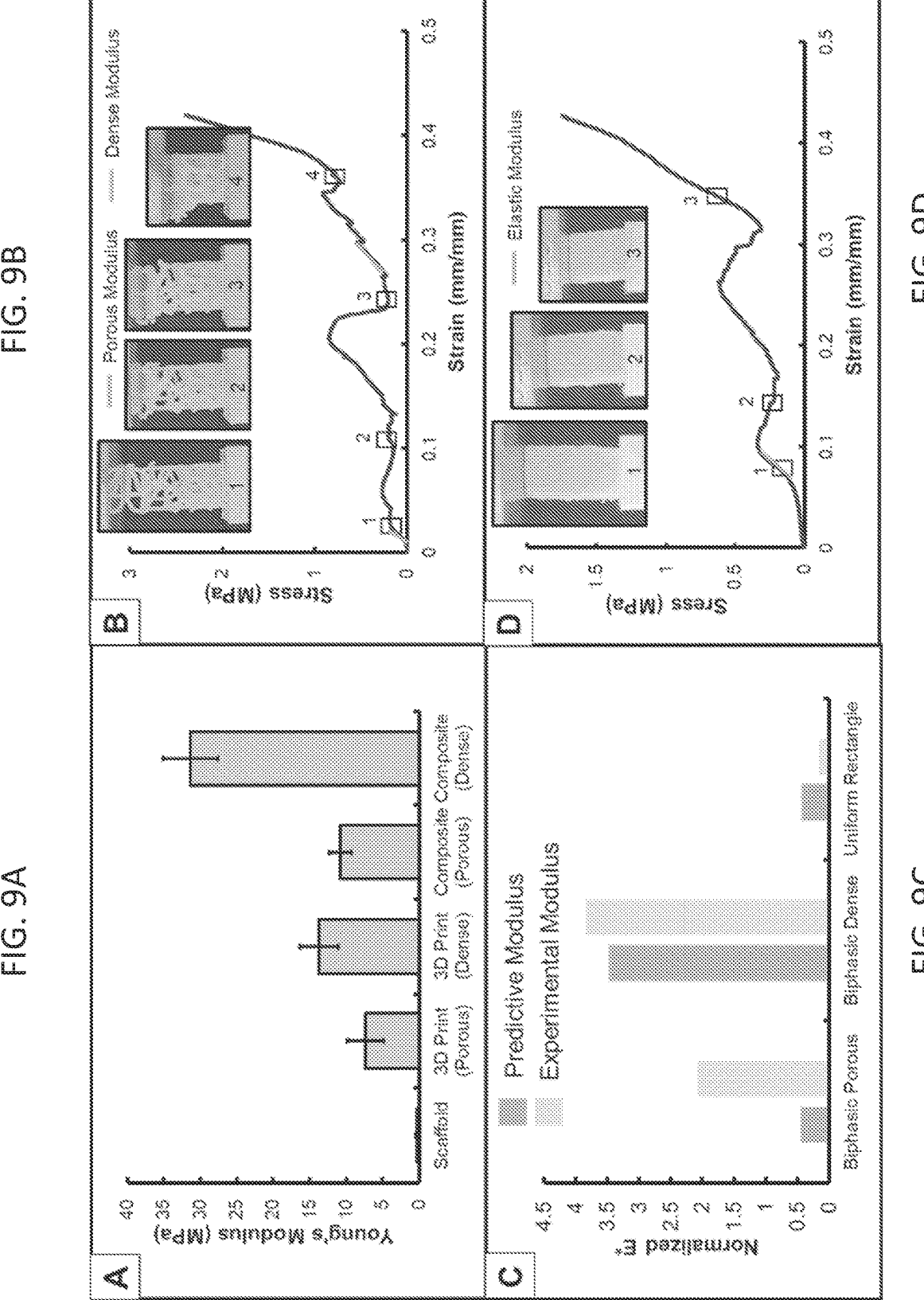
FIGS. 9A-9D show additional mechanics of mineralized collagen scaffolds reinforced with a biphasic Voronoi 3D-print.
Figure 10:
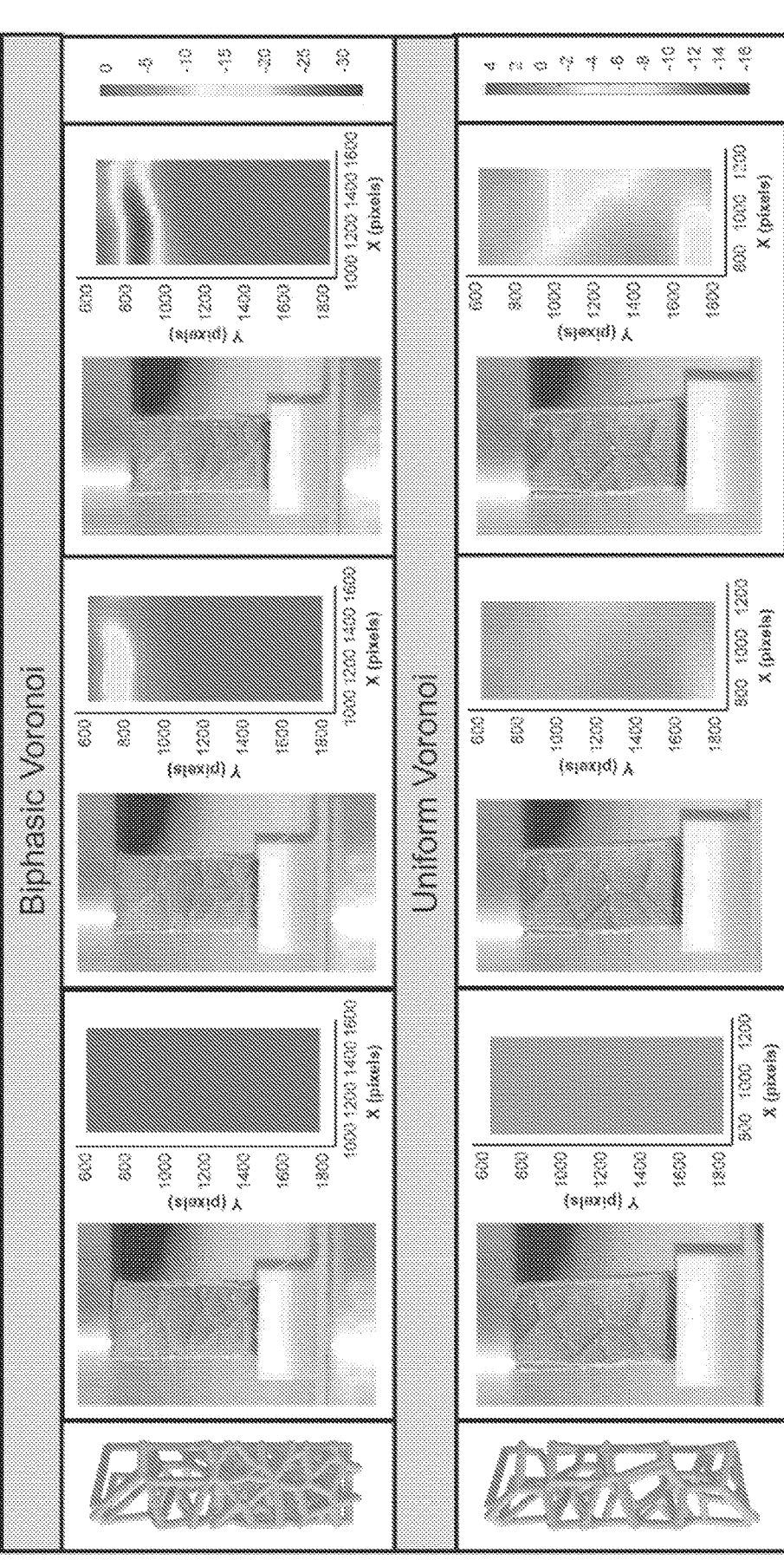
FIG. 10 illustrates stress-strain profiles of uniform and biphasic Voronoi-mineralized collagen composites. Biphasic and uniform Voronoi composites were compressed and images during compression were analyzed for localized strain (n=6, representative images). Images of the composites are displayed with increasing compression and matching strain profiles in the direction of compression (y axis). Red indicates low strain and blue indicated regions of high strain. Biphasic Voronoi structures are oriented with the more porous region in contact with the compression platen (top of profile and images). Composites measured 20 mm×6 mm×6 mm (length×height×width).

Mineralized collagen scaffolds were combined with biphasic Voronoi 3D-prints as well as uniform Voronoi 3D-prints made of white photopolymerized resin. During compression of biphasic 3D-prints without collagen, there was a porous 3D-print compressive region and a dense 3D-print compression region visible on stress-strain curves (FIG. 8A). Within each of these dense and porous print regions, an elastic regime, collapsed plateau, and densification regime was visible (FIG. 8B). SEM analysis demonstrated that in the more porous regions of the biphasic composite material, there was good integration between the 3D-print and collagen scaffold (FIG. 9). In the denser regions of the biphasic composite material, there were some empty spaces where collagen was unable to fully penetrate due to the small pores and high density of the dense region of the 3D-print. A similar dense and porous 3D-print moduli regime was visible in the biphasic Voronoi-mineralized collagen composites, and the addition of mineralized collagen added an increased Young's Modulus in the porous and dense region compared to the 3D-print alone (FIGS. 8A and 8B). Additionally, it was more difficult to predict the moduli of the rectangular Voronoi 3D-print, as the experimentally determined porous region moduli of the biphasic print was much higher than the predictive moduli (FIGS. 9A-9D). DIC testing of the uniform and biphasic Voronoi composites demonstrated that biphasic composites had strain localization in the porous region only, while uniform composites had strain localization randomly throughout the structure (FIG. 10). This region of strain was also more intense (higher strain), in the biphasic composite than the uniform composite.

Example 4

Lanalysis of Push-Out Force 2D and 3D Voronoi composite sheets were compared to mineralized collagen scaffolds in a push-out test with two defect sizes (11.5 mm and 10.8 mm). Both the 2D and 3D Voronoi 3D-prints were well integrated into the surrounding mineralized collagen scaffold with no empty spaces or holes (FIG. 12A, FIG. 13). 12 mm cylindrical specimens were added to two smaller cylindrical defects and the maximum force achieved to push these through a Teflon mold was measured. There were no differences in push-out force between the mineralized collagen scaffold and the 2D Voronoi composite (FIG. 12B). Additionally, both the mineralized collagen scaffold and 2D Voronoi composite did not require significantly (p<0.05) greater force to push through the 11.5 mm defect and the 10.8 mm defect. The 3D Voronoi composite did have significantly (p<0.003, p<0.00005) greater force required to push it through the 11.5 mm defect and 10.8 mm defect, respectively, than the mineralized collagen scaffold. Additionally, pushing the 3D Voronoi composite through the 10.8 mm defect required significantly (p<0.02) greater force than the 11.5 mm defect. Although mineralized collagen scaffolds were tested with two different thicknesses to better compare to the dimensions of the 2D and 3D Voronoi composites, there were no significant (p<0.05) differences in the push-out force required of these different thicknesses in the 11.5 or 10.8 mm defects. To note, the 2D Voronoi composites were more difficult to add to the Teflon mold due their stiff nature compared to the 3D Voronoi composites, which were easily deformable.

Example 5

In Vivo Testing of Composite Material

This example describes experiments for testing use of a disclosed composite material to repair a bone defect in an in vivo rabbit model. One skilled in the art will appreciate that methods that deviate from these specific methods can also be used to treat a bone defect in vivo.

Approximately three weeks prior to creation of the parietal defect, 26 female New Zealand White rabbits (2-3 months old) undergo bone marrow harvest from the ilium. Preoperatively, rabbits are injected subcutaneously with enrofloxacin (5 mg/kg) and acepromazine (1 mg/kg). Anesthesia is maintained with isoflurane gas (1.5-3%) during the procedure and pain control is performed with buprenorphine 0.05 mg/kg and carprofen 4 mg/kg subcutaneous injection. Isolated BMSCs are cultured and $2 \times 10^6$ cells are seeded onto scaffolds in proliferation media. 24 hours after seeding, proliferation media is exchanged for osteogenic differentiation media consisting of 10 mM B-glycerophosphate, 50 µg/ml ascorbic acid and 0.1 µM dexamethasone. Scaffolds are untreated or treated with rhBMP-2 at a concentration of 50 ng/mL for one week. Media and BMP-2 are changed every 2-3 days.

The head of each rabbit is shaved and disinfected with Betadine. The cranial surface is exposed by a midline incision and the overlying parietal periosteum is dissected off of the calvarium. For each rabbit, a 14 mm full thickness, extradural defect is created by a hand powered trephine and the bone is lifted away without injury to the dura. One scaffold is implanted for each rabbit and the incision is closed with sutures.

Twelve weeks after implantation, the rabbits are euthanized by intravenous injection of 1 mL of pentobarbital solution (Fatal-Plus®, 390 mg/ml) intravenously via the marginal ear vein. The previous incision is then reopened and the calvarium is exposed. The calvarium including the cranial defect is analyzed grossly and then explanted for micro-CT, histologic, and biomechanical analyses. Gene expression and "push-out" testing may also be performed.

In view of the many possible embodiments to which the principles of the disclosure may be applied, it should be recognized that the illustrated embodiments are only examples and should not be taken as limiting the scope of the disclosure nor the claims. Rather, the scope of the claimed subject matter is defined by the following claims and their equivalents.

We claim:

1. A composite material comprising:
   a macroporous structure having a Voronoi architecture, the macroporous structure comprising a deformable mesh comprising a plurality of pores;
   a microporous biomaterial integrated into the macroporous structure; and
   wherein the macroporous structure is configured to achieve conformal shape-fitting via the deformable mesh when implanted within a bone defect.

2. The composite material of claim 1, wherein the mesh comprises pores of at least about 0.5 mm in at least one dimension.

3. The composite material of claim 1, wherein the macroporous structure comprises fibers connecting points defining the Voronoi architecture.

4. The composite material of claim 3, wherein the fibers have a diameter of about 10 µm to about 2 mm.

5. The composite material of claim 1, wherein the macroporous structure comprises at least a first portion and a second portion, and wherein the pore size of the first portion is greater than the pore size of the second portion.

6. The composite material of claim 5, wherein a ratio of the pore size of the first portion to the second portion is up to about 10:1.

7. The composite material of claim 1, wherein the macroporous structure is a two-dimensional structure having a first surface and a second surface.

8. The composite material of claim 1, wherein the macroporous structure is a three-dimensional structure.

9. The composite material of claim 1, wherein the macroporous structure is isotropic or anisotropic.

10. The composite material of claim 1, wherein the macroporous structure has a Young's modulus between 100 kPa and 250 MPa.

11. The composite material of claim 1, wherein the macroporous structure is capable of elastic deformation for up to 20% of applied strain, plastic deformation for up to 80% strain, or both.

12. The composite material of claim 1, wherein the biomaterial comprises collagen, glycosaminoglycans, calcium phosphate, or a combination of two or more thereof.

13. The composite material of claim 1, wherein the biomaterial is not covalently linked to the macroporous structure.

14. The composite material of claim 1, wherein the biomaterial is covalently linked to the macroporous structure.

15. A method of treating a bone defect, comprising:
    implanting a composite material comprising a macroporous structure having a Voronoi architecture and a microporous biomaterial integrated into the macroporous structure in a bone defect in a subject, wherein the macroporous structure comprises a deformable mesh comprising a plurality of pores and wherein the deformable mesh allows the macroporous structure to achieve conformal shape-fitting within the bone defect.

16. The method of claim 15, further comprising shaping the composite material to the bone defect prior to implanting the composite material in the subject.

17. The method of claim 15, further comprising hydrating the composite material in a sterile solution prior to implanting in the subject.

* * * * *